United States Patent
Mizuki et al.

(10) Patent No.: US 11,616,201 B2
(45) Date of Patent: Mar. 28, 2023

(54) SPECIFIC LADDER TYPE COMPOUNDS FOR ORGANIC LIGHT EMITTING DEVICES

(71) Applicant: Idemitsu Kosan Co., Ltd., Chiyoda-ku (JP)

(72) Inventors: Yumiko Mizuki, Basel (CH); Francois Rime, Delemont (CH); Natalia Chebotareva, Hagenthal le Bas (FR); Hideaki Nagashima, Basel (CH)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 741 days.

(21) Appl. No.: 16/488,500

(22) PCT Filed: Feb. 23, 2018

(86) PCT No.: PCT/IB2018/051139
§ 371 (c)(1),
(2) Date: Aug. 23, 2019

(87) PCT Pub. No.: WO2018/154501
PCT Pub. Date: Aug. 30, 2018

(65) Prior Publication Data
US 2020/0381628 A1    Dec. 3, 2020

(30) Foreign Application Priority Data
Feb. 24, 2017    (EP) .................................... 17157829

(51) Int. Cl.
*H01L 51/00*    (2006.01)
*C09K 11/06*    (2006.01)
(Continued)

(52) U.S. Cl.
CPC ...... *H01L 51/0067* (2013.01); *C07D 491/048* (2013.01); *C09K 11/06* (2013.01);
(Continued)

(58) Field of Classification Search
CPC ............. H01L 51/0067; H01L 51/0085; H01L 51/0087; H01L 51/0088; H01L 51/0071; H01L 51/5072; C09K 11/06
(Continued)

(56) References Cited

U.S. PATENT DOCUMENTS

2012/0068170 A1    3/2012    Pflumm et al.
2012/0097899 A1    4/2012    Parham et al.
(Continued)

FOREIGN PATENT DOCUMENTS

KR    10-2015-0141147    12/2015
WO    WO 2011/000455 A1    1/2011
(Continued)

OTHER PUBLICATIONS

International Search Report dated May 16, 2018 in PCT/IB2018/051139 filed Feb. 23, 2018.

*Primary Examiner* — Thinh T Nguyen
(74) *Attorney, Agent, or Firm* — Oblon, McClelland, Maier & Neustadt, L.L.P.

(57) ABSTRACT

The present invention relates to a compound of formula (I), wherein $R^1$, $R^2$, $R^3$ and $R^4$ are each independently hydrogen or $R^a$, with proviso that a pair of two substituents selected from $R^1$ and $R^2$, $R^2$ and $R^3$, and $R^3$ and $R^4$ is linked to one another and forms a group of formula (II); a material for an organic electroluminescence device comprising at least one compound of formula (I); an organic electroluminescence device which comprises an organic thin film layer be-tween an anode and a cathode, wherein the organic thin film layer comprises one or more layers and comprises a light emitting layer, and at least one layer of the organic thin film layer comprises at least one compound of formula (I); and an electronic equipment comprising the inventive organic electroluminescence device.

(Continued)

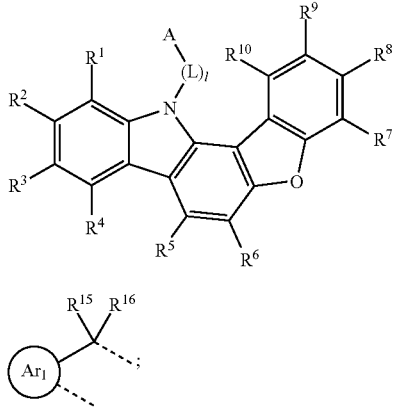

15 Claims, 1 Drawing Sheet

(51) Int. Cl.
*C07D 491/048* (2006.01)
*H01L 51/50* (2006.01)

(52) U.S. Cl.
CPC ...... H01L 51/0071 (2013.01); H01L 51/0085 (2013.01); H01L 51/0087 (2013.01); H01L 51/0088 (2013.01); C09K 2211/185 (2013.01); H01L 51/5016 (2013.01); H01L 51/5072 (2013.01)

(58) Field of Classification Search
USPC ........................................ 257/40; 438/82, 99
See application file for complete search history.

(56) References Cited

U.S. PATENT DOCUMENTS

2014/0138669 A1* 5/2014 Nakagawa et al. .......................... H01L 51/0056 428/690
2015/0034914 A1 2/2015 Lee et al.
2015/0337197 A1 11/2015 Jatsch et al.
2017/0062732 A1 3/2017 Jatsch et al.
2017/0200904 A1 7/2017 Lee et al.

FOREIGN PATENT DOCUMENTS

WO  WO 2013/105747 A1  7/2013
WO  WO 2014/094963 A1  6/2014
WO  WO 2015/124255 A1  8/2015

* cited by examiner

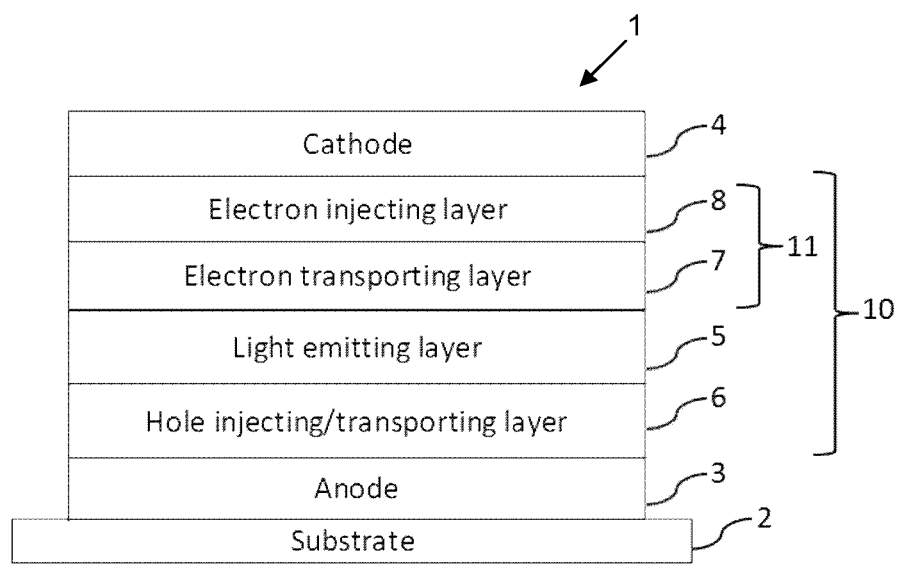

SPECIFIC LADDER TYPE COMPOUNDS FOR ORGANIC LIGHT EMITTING DEVICES

The present invention relates to specific ladder type compounds and organic electroluminescence devices comprising the same.

US 2015/0034914 A1 relates to organic compounds represented by a combination of a moiety represented by the following Chemical Formula 1, a moiety represented by the following Chemical Formula 2, and a moiety represented by the following Chemical Formula 3:

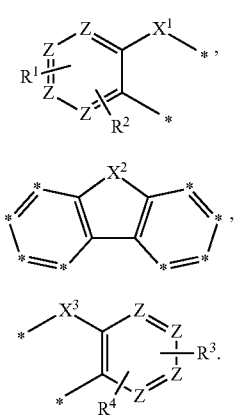

(Chemical Formula 1)

(Chemical Formula 2)

(Chemical Formula 3)

US 2015/0034914 A1 further relates to an organic optoelectric device including an anode and a cathode facing each other, and at least one organic layer interposed between the anode and the cathode, the organic layer including an organic compound as described above, and to a display device including an organic optoelectric device as described above. However, US 2015/0034914 A1 does not disclose the following specific combination of heteroatoms/groups in the ladder structures described in US 2015/0034914 A1: N, O and

US 2012/0068170 A1 relates to indenocarbazole derivatives having electron- and hole-transporting properties, in particular for use in the emission and/or charge-transport layer of electroluminescent devices or as matrix material. The invention furthermore relates to a process for the preparation of said compounds and to electronic devices comprising same. However, US 2012/0068170 A1 does not disclose ladder structures comprising at least seven condensed rings and also does not disclose the following specific combination of heteroatoms/groups in the structures described in US 2012/0068170 A1: N, O and

Further, US 2012/0068170 A1 does not mention the specific connection of the condensed rings as claimed in the present application.

WO 2011/000455 A1 relates to indenocarbazole derivatives which can preferably be employed as matrix materials for phosphorescent dopants or as electron-transport materials, in particular for use in the emission and/or charge-transport layer of electroluminescent devices. The invention furthermore relates to polymers which comprise these compounds as structural units and to a process for the preparation of said compounds and to electronic devices which comprise these compounds. However, WO 2011/000455 A1 does not disclose the following specific combination of heteroatoms/groups in the structures described in WO 2011/000455 A1: N, O and

Further, WO 2011/000455 A1 does not mention the specific connection of the condensed rings as claimed in the present application.

WO 2015/124255 A1 relates to materials for use in electronic devices, especially in organic electroluminescent devices and electronic devices, especially in organic electroluminescent devices comprising said materials. The materials have one of the following formulae:

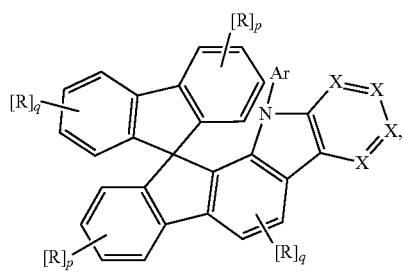

formula (1)

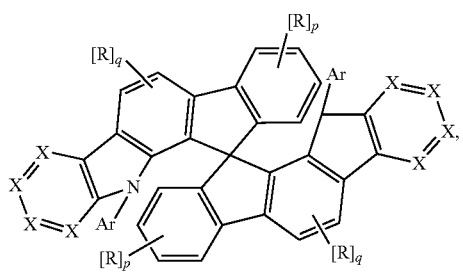

formula (2)

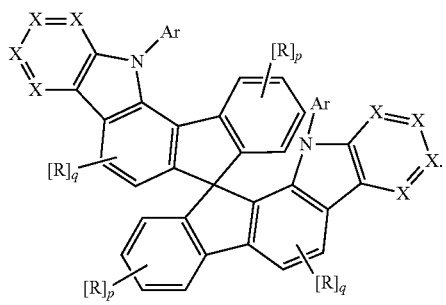

formula (3)

However, WO 2015/124255 A1 does not exemplify the following specific combination of heteroatoms/groups in the structures described in WO 2015/124255 A1: N, O and

WO 2014/094963 A1 relates to materials for use in electronic devices, in particular in organic electroluminescent devices, and to electronic devices, in particular organic electroluminescent devices, comprising these materials. The materials have one of the following formulae:

formula (1)

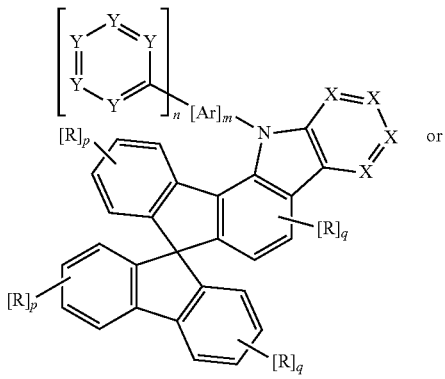

formula (1A)

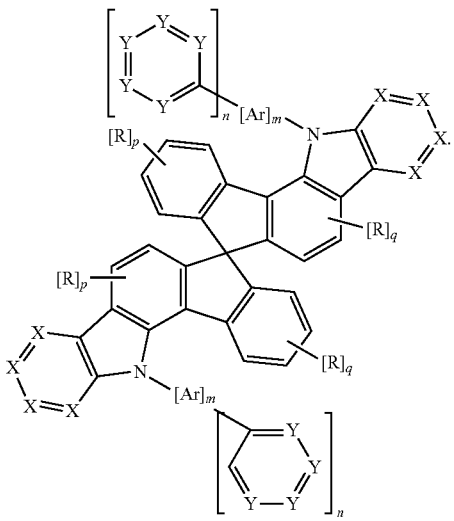

However, WO 2014/94963 A1 does not exemplify the following specific combination of heteroatoms/groups in the structures described in WO 2015/124255 A1: N, O and having the specific connection of the condenses rings as claimed in the present application. A1 does not exemplify the following specific combination of heteroatoms/groups in the structures described in WO 2015/124255 A1: N, O and

having the specific connection of the condensed rings as claimed in the present application.

Notwithstanding these developments, there remains a need for organic light emitting devices comprising new materials, especially host (=matrix) materials, charge transport materials, i.e. hole transport materials and electron transport materials, and/or charge/exciton blocker materials, i.e. electron/exciton blocker materials and hole/exciton blocker materials, to provide improved performance of electroluminescent devices.

Accordingly, it is an object of the present invention, with respect to the aforementioned documents, to provide further materials suitable for use in organic electronic devices and further applications in organic electronics. More particularly, it should be possible to provide charge transport materials, i.e. hole transport materials and electron transport materials, and/or charge/exciton blocker materials, i.e. electron/exciton blocker materials and hole/exciton blocker materials, and host (=matrix) materials for use in organic electronic devices. The materials should be suitable especially for organic electronic devices which comprise at least one emitter, which is a phosphorescence emitter and/or a fluorescence emitter, preferably a phosphorescence emitter, for example at least one green emitter.

Furthermore, the materials should be suitable for providing organic electronic devices which ensure good performance of the organic electronic devices, especially good operative lifetimes, and/or a low use and operating voltage of the organic electronic devices.

Said object is solved by a compound of formula (1)

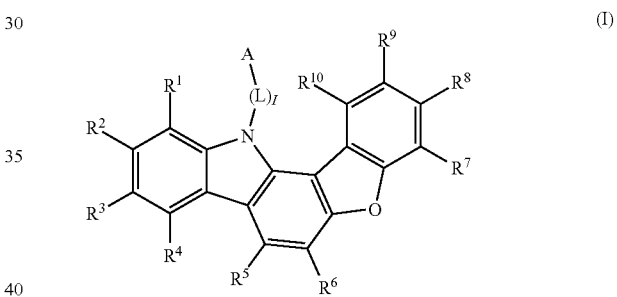

wherein
$R^1$, $R^2$, $R^3$ and $R^4$ are each independently hydrogen or $R^a$, with proviso that a pair of two substituents selected from $R^1$ and $R^2$, $R^2$ and $R^3$, and $R^3$ and $R^4$ is linked to one another and forms a group of formula (II)

(II)

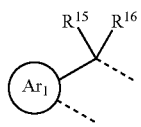

wherein
$Ar_1$ represents a substituted or unsubstituted aromatic hydrocarbon group having 6 to 30 ring carbon atoms or a substituted or unsubstituted heterocyclic group having 5 to 30 ring atoms, the dotted lines are bonding sites;
$R^5$, $R^6$, $R^7$, $R^8$, $R^9$, $R^{10}$, $R^{15}$, $R^{16}$ and $R^a$
are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

$R^{15}$ and $R^{16}$ may be bonded to each other to form a ring structure;

two or more substituents selected from $R^a$, $R^5$, $R^6$, $R^7$, $R^8$, $R^9$ and $R^{10}$ may be bonded to each other to form a ring structure;

A is a substituted or unsubstituted aromatic hydrocarbon group having 6 to 30 ring carbon atoms; or a substituted or unsubstituted heterocyclic group having 5 to 30 ring atoms, or a disubstituted amino group;

L is a single bond, a substituted or unsubstituted alkylene group having 1 to 30 carbon atoms, a substituted or unsubstituted cycloalkylene group having 3 to 30 carbon atoms, a substituted divalent silyl group having 2 to 30 carbon atoms, a substituted or unsubstituted divalent aromatic hydrocarbon group having 6 to 30 ring carbon atoms, or a substituted or unsubstituted divalent heterocyclic group having 5 to 30 ring atoms;

l is 0, 1, 2 or 3.

The ladder type compounds of formula (I) according to the present invention are specific in view of the connection of the at least seven rings and in view of the combination of heteroatoms present in the ladder type structure.

The specific ladder type compounds according to formula (I) give rise to materials, especially host, charge transport or charge blocking materials, that are highly suitable in organic electronic devices that emit for example red, blue or green light. Moreover, a balanced charge transport, i.e. hole transport or electron transport, and/or charge/exciton blocking, i.e. electron/exciton blocking or hole/exciton blocking, in devices is achieved, especially resulting in low voltages and/or long lifetimes.

The compounds of the present invention may be used in organic electronic devices such as electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and organic electroluminescent devices, for example, organic light-emitting diodes (OLEDs).

Accordingly, a further subject of the present invention is directed to an organic electronic device, comprising a compound according to the present invention. The organic electronic device is preferably an electroluminescent device (EL device), such as an organic light-emitting diode (OLED).

The compounds of formula (I) can in principal be used in any layer of an EL device, but are preferably used as host, charge transport, i.e. hole transport or electron transport, and/or charge/exciton blocking, i.e. electron/exciton blocking or hole/exciton blocking, material. Particularly, the compounds of formula (I) are used as host material for red, blue or green light emitting phosphorescence or fluorescence emitters, preferably green phosphorescence emitters. Further, the compounds of formula (1) are particularly suitable as electron transporting and/or hole blocking material in fluorescent or phosphorescent EL devices.

Hence, a further subject of the present invention is directed to an emitting layer, comprising a compound of formula (I) according to the present invention. In said embodiment a compound of formula (I) is preferably used as host material or as co-host material together with one or more, preferably one, further host materials. More preferably, a combination of a compound of formula (I) as host material or as co-host material together with a phosphorescent emitter is used.

The terms aromatic hydrocarbon group having 6 to 30 ring carbon atoms, heterocyclic group having 5 to 30 ring atoms, alkyl group having 1 to 30 carbon atoms, cycloalkyl group having 3 to 30 carbon atoms, aralkyl group having 7 to 31 carbon atoms, alkylene group having 1 to 30 carbon atoms, cycloalkylene group having a ring structure formed of 3 to 30 carbon atoms, divalent silyl group having 2 to 30 carbon atoms, divalent aromatic hydrocarbon group having a ring structure formed of 6 to 30 carbon atoms, divalent heterocyclic group having a ring structure formed of 5 to 30 atoms, mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms, halogen atom, alkoxy group having 1 to 30 carbon atoms, haloalkyl group having 1 to 30 carbon atoms, haloalkoxy group having 1 to 30 carbon atoms, aryloxy group having 6 to 30 ring carbon atoms, alkylthio group having 1 to 30 carbon atoms, arylthio group having 6 to 30 ring carbon atoms, alkenyl group having 2 to 30 carbon atoms, di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms, cyano group, nitro group, sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms, di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms, alkylcarbonyloxy group having 2 to 31 carbon atoms, arylcarbonyloxy group having 6 to 30 ring carbon atoms, boron-containing group are known in the art and generally have the following meaning, if said groups are not further specified in specific embodiments mentioned below:

The aromatic hydrocarbon group having 6 to 30 ring carbon atoms, preferably 6 to 18 ring carbon atoms, may be a non-condensed aromatic hydrocarbon group or a condensed aromatic hydrocarbon group. Specific examples thereof include phenyl group, naphthyl group, phenanthryl group, biphenyl group, terphenyl group, quaterphenyl group, fluoranthenyl group, triphenylenyl group, phenanthrenyl group, fluorenyl group, spirofluorenyl group, 9,9-diphenylfluorenyl group, 9,9'-spirobi[9H-fluorene]-2-yl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, and benzo[b]fluoranthenyl group, with phenyl group, naphthyl group, biphenyl group, terphenyl group, phenanthryl group, triphenylenyl group, fluorenyl group, spirobifluorenyl group, and fluoranthenyl group being preferred, and phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group being more preferred.

The heterocyclic group having 5 to 30 ring atoms, preferably 5 to 18 ring atoms, may be a non-condensed heterocyclic group or a condensed heterocyclic group. Specific examples thereof include the residues of pyrrole ring, isoindole ring, benzofuran ring, isobenzofuran ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyran ring, dibenzofuran ring, and benzo[c]dibenzofuran ring, and the residues of derivatives of these rings, with the residues of triazine ring, dibenzofuran ring, carbazole ring, dibenzothiophene ring, and derivatives of these rings being preferred, and the residues of triazine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group being more preferred.

Examples of the alkyl group having 1 to 30 carbon atoms include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, with methyl group, ethyl group, n-propyl group, isopropyl group, n-butyl group, s-butyl group, isobutyl group, t-butyl group being preferred.

Examples of the cycloalkyl group having 3 to 30 carbon atoms include cyclopropyl group, cyclobutyl group, cyclopentyl group, cyclohexyl group, cyclooctyl group, and adamantyl group, with cyclopentyl group, and cyclohexyl group being preferred.

Examples of the aralkyl group having 7 to 31 carbon atoms, preferably 7 to 20 carbon atoms, include benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, 3-naphthylmethyl group, 1-β-naphthylethyl group, 2-3-naphthylethyl group, 1-β-naphthylisopropyl group, 2-β-naphthylisopropyl group, 1-pyrrolylmethyl group, 2-(1-pyrrolyl)ethyl group, β-methylbenzyl group, m-methylbenzyl group, o-methylbenzyl group, β-chlorobenzyl group, m-chlorobenzyl group, o-chlorobenzyl group, β-bromobenzyl group, m-bromobenzyl group, o-bromobenzyl group, β-iodobenzyl group, m-iodobenzyl group, o-iodobenzyl group, β-hydroxybenzyl group, m-hydroxybenzyl group, o-hydroxybenzyl group, β-aminobenzyl group, m-aminobenzyl group, o-aminobenzyl group, β-nitrobenzyl group, m-nitrobenzyl group, o-nitrobenzyl group, β-cyanobenzyl group, m-cyanobenzyl group, o-cyanobenzyl group, 1-hydroxy-2-phenylisopropyl group, and 1-chloro-2-phenylisopropyl group.

Examples of the alkylene group (i.e. alkane-diyl group) having 1 to 30 carbon atoms represented include methylene group, ethylene group, n-propylene group, isopropylene group, n-butylene group, s-butylene group, isobutylene group, t-butylene group, n-pentylene group, n-hexylene group, n-heptylene group, n-octylene group, n-nonylene group, n-decylene group, n-undecylene group, n-dodecylene group, n-tridecylene group, n-tetradecylene group, n-pentadecylene group, n-hexadecylene group, n-heptadecylene group, n-octadecylene group, neopentylene group, 1-methylpentylene group, with methylene group, ethylene group, n-propylene group, isopropylene group, n-butylene group, s-butylene group, isobutylene group, t-butylene group being preferred.

Examples of the cycloalkylene group (i.e. cycloalkane-diyl group) having 3 to 30 carbon atoms include cyclopropylene group, cyclobutylene group, cyclopentylene group, cyclohexylene group, cyclooctylene group, and adamantylene group, with cyclopentylene group, and cyclohexylene group being preferred.

Examples of the divalent silyl group having 2 to 30 carbon atoms include divalent trimethylsilyl group, divalent triethylsilyl group, divalent tributylsilyl group, divalent dimethylethylsilyl group, divalent t-butyldimethylsilyl group, divalent vinyldimethylsilyl group, divalent propyldimethylsilyl group, divalent dimethylisopropylsilyl group, divalent dimethylpropylsilyl group, divalent dimethylbutylsilyl group, divalent dimethyltertiarybutylsilyl group, divalent diethylisopropylsilyl group, divalent phenyldimethylsilyl group, divalent diphenylmethylsilyl group, divalent diphenyltertiarybutylsilyl group, and divalent triphenylsilyl group, with divalent trimethylsilyl group, divalent triethylsilyl group, divalent t-butyldimethylsilyl group, divalent vinyldimethylsilyl group, and divalent propyldimethylsilyl group being preferred.

The divalent aromatic hydrocarbon group having 6 to 30 ring carbon atoms may be a non-condensed divalent aromatic hydrocarbon group or a condensed divalent aromatic hydrocarbon group. Specific examples thereof include phenylene group, naphthylene group, phenanthrylene group, biphenyl-diyl group, terphenyl-diyl group, quaterphenyl-diyl group, fluoranthen-diyl group, triphenylene-diyl group, phenanthrene-diyl group, fluorene-diyl group, spirofluorene-diyl group, 9,9-diphenylfluorene-diyl group, 9,9'-spirobi[9H-fluorene]-2-diyl group, 9,9-dimethylfluorene-diyl group, benzo[c]phenanthrene-diyl group, benzo[a]triphenylene-diyl group, naphtho[1,2-c]phenanthrene-diyl group, naphtho[1,2-a]triphenylenylene-diyl group, dibenzo[a,c]triphenylenylene-diyl group, and benzo[b]fluoranthene-diyl group, with phenylene group, naphthylene group, biphenyl-diyl group, terphenyl-diyl group, phenanthryl-diyl group, triphenylenylen-diyl group, fluorene-diyl group, spirobifluorene-diyl group, and fluoranthene-diyl group being preferred, and 1,2-phenylene group, 1,3-phenylene group, 1,4-phenylene group, 1,4-naphthylene group, 1,8-naphthylene group, 2,6-naphthylene group, 2,7-naphthylene group, biphenyl-2,2'-diyl group, biphenyl-2,3'-diyl group, biphenyl-2,4'-diyl group, biphenyl-2,5'-diyl group, biphenyl-2,6'-diyl group, biphenyl-3,3'-diyl group, biphenyl-3,4'-diyl group, biphenyl-3,5'-diyl group, biphenyl-3,6'-diyl group, biphenyl-4,4'-diyl group, biphenyl-4,5'-diyl group, biphenyl-4,6'-diyl group, biphenyl-5,5'-diyl group, biphenyl-5,6'-diyl group, biphenyl-6,6'-diyl group, phenanthrene-9,10-diyl group, phenanthrene-2,3-diyl group, phenanthrene-2,7-diyl group, phenanthrene-2,8-diyl group, phenanthrene-2,6-diyl group, phenanthrene-2,9-diyl group, phenanthrene-2,10-diyl group, phenanthrene-3,9-diyl group, phenanthrene-3,10-diyl group, triphenylene-2,3-diyl group, triphenylene-2,5-diyl group, triphenylene-2,6-diyl group, triphenylene-2,7-diyl group, triphenylene-2,8-diyl group, 9,9-dimethylfluorene-2,7-diyl group, 9,9-dimethylfluorene-3,7-diyl group, 9,9-dimethylfluorene-1,4-diyl group, fluoranthene-3,9-diyl group, fluoranthene-3,8-diyl group, fluoranthene-3,4-diyl group, fluoranthene-3,5-diyl group, fluoranthene-3,6-diyl group, fluoranthene-2,9-diyl group, fluoranthene-2,8-diyl group, fluoranthene-2,4-diyl group, fluoranthene-2,5-diyl group, fluoranthene-2,6-diyl group, fluoranthene-1,9-diyl group, fluoranthene-1,8-diyl group, fluoranthene-1,4-diyl group, fluoranthene-1,5-diyl group, fluoranthene-1,6-diyl group being more preferred.

The divalent heterocyclic group having 5 to 30 ring atoms may be a non-condensed heterocyclic group or a condensed heterocyclic group. Specific examples thereof include the divalent residues of pyrrole ring, isoindole ring, benzofuran ring, isobenzofuran ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyran ring, dibenzofuran ring, and benzo[c]dibenzofuran ring, and the divalent residues of derivatives of these rings, with the divalent residues of dibenzofuran ring, carbazole ring, dibenzothiophene ring, and derivatives of these divalent rings being preferred, and the dibenzofuran-diyl group, 9-phenylcarbazole-diyl group and dibenzothiophene-diyl group being more preferred.

Examples of mono-, di-, or tri-substituted silyl groups having a substituent selected from a group consisting of a substituted or unsubstituted alkyl group having 1 to 30 carbon atoms and a substituted or unsubstituted aromatic hydrocarbon group having 6 to 30 ring carbon atoms include alkylsilyl groups having 1 to 10 carbon atoms, preferably 1 to 5 carbon atoms, including trimethylsilyl group, triethylsilyl group, tributylsilyl group, dimethylethylsilyl group, t-butyldimethylsilyl group, vinyldimethylsilyl group, propyldimethylsilyl group, dimethylisopropylsilyl group, dimethylpropylsilyl group, dimethylbutylsilyl group, dimethyltertiarybutylsilyl group, diethylisopropylsilyl group, and arylsilyl groups having 6 to 30 carbon atoms, preferably 6 to 18 carbon atoms, including phenyldimethylsilyl group, diphenylmethylsilyl group, diphenyltertiarybutylsilyl group, and triphenylsilyl group, with trimethylsilyl group, triethylsilyl group, t-butyldimethylsilyl group, vinyldimethylsilyl group, and propyldimethylsilyl group being preferred.

Examples of halogen atoms include fluorine, chlorine, bromine, and iodine, with fluorine being preferred.

Examples of the alkoxy group having 1 to 30 carbon atoms include those having an alkyl portion selected from the alkyl groups mentioned above.

Examples of the haloalkyl group having 1 to 30 carbon atoms include the alkyl groups mentioned above wherein the hydrogen atoms thereof are partly or entirely substituted by halogen atoms.

Examples of a haloalkoxy group having 1 to 30 carbon atoms include the alkoxyl group mentioned above wherein the hydrogen atoms thereof are partly or entirely substituted by halogen atoms.

Examples of an aryloxy group having 6 to 30 ring carbon atoms include those having an aryl portion selected from the aromatic hydrocarbon groups mentioned above.

Examples of an alkylthio group having 1 to 30 carbon atoms include those having an alkyl portion selected from the alkyl groups mentioned above.

Examples of an arylthio group having 6 to 30 ring carbon atoms include those having an aryl portion selected from the aromatic hydrocarbon groups mentioned above.

Examples of alkenyl groups having 2 to 30 carbon atoms are alkyl groups comprising one or more, preferably one or two, more preferably one double bond(s) in the alkyl chain, including for example ethenyl group, n-propenyl group, n-butenyl group, s-butenyl group, isobutenyl group, n-pentenyl group, n-hexenyl group, n-heptenyl group, n-octenyl group, n-nonenyl group, n-decenyl group, n-undecenyl group, n-dodecenyl group, n-tridecenyl group, n-tetradecenyl group, n-pentadeencyl group, n-hexadecenyl group, n-heptadecenyl group, n-octadecenyl group, neopentenyl group, 1-methylpentenyl group, with ethenyl group, n-propenyl group, n-butenyl group, s-butenyl group, isobutenyl group being preferred.

An amino group generally has the formula —$NH_2$.

Examples of di-substituted amino groups having a substituent selected from the group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms generally have the formula —$NR'_2$, wherein the residues R' may be identical or different and are independently of each other a substituted or unsubstituted alkyl group having 1 to 30 carbon atoms or a substituted or unsubstituted aromatic hydrocarbon group having 6 to 30 ring carbon atoms, wherein preferred alkyl groups having 1 to 30 carbon atoms and preferred aromatic hydrocarbon groups having 6 to 30 ring carbon atoms are mentioned above. Preferably R' is a substituted or unsubstituted hydrocarbon group having 6 to 30 ring carbon atoms or a substituted or unsubstituted heterocyclic group having 5 to 30 ring atoms.

A cyano group generally has the formula —C≡N.

A nitro group generally has the formula —$NO_2$.

Examples of sulfonyl groups having a substituent selected from the group consisting of a substituted or unsubstituted alkyl group having 1 to 30 carbon atoms and a substituted or unsubstituted aromatic hydrocarbon group having 6 to 30 ring carbon atoms generally have the formula —$SO_2R'$, wherein R' is a substituted or unsubstituted alkyl group having 1 to 30 carbon atoms or a substituted or unsubstituted aromatic hydrocarbon group having 6 to 30 ring carbon atoms, wherein preferred alkyl groups having 1 to 30 carbon atoms and preferred aromatic hydrocarbon groups having 6 to 30 ring carbon atoms are mentioned above.

Examples of di-substituted phosphoryl groups having a substituent selected from the group consisting of a substituted or unsubstituted alkyl group having 1 to 30 carbon atoms and a substituted or unsubstituted aromatic hydrocarbon group having 6 to 30 ring carbon atoms generally have the formula —P(=O)R'R", wherein R' and R" are each independently a substituted or unsubstituted alkyl group having 1 to 30 carbon atoms or a substituted or unsubstituted aromatic hydrocarbon group having 6 to 30 ring carbon atoms, wherein preferred alkyl groups having 1 to 30 carbon atoms and preferred aromatic hydrocarbon groups having 6 to 30 ring carbon atoms are mentioned above. Preferably, R' and R" are a substituted or unsubstituted aromatic hydrocarbon group having 6 to 30 carbon atoms, more preferably R' and R" are phenyl, i.e. the phosphoryl group is a diphenylphosphine oxide group.

Examples of alkylcarbonyloxy groups having 2 to 31 carbon atoms generally have the formula —C(=O)OR', wherein R' is a substituted or unsubstituted alkyl group having 1 to 30 carbon atoms wherein preferred alkyl groups having 1 to 30 carbon atoms are mentioned above.

Examples of arylcarbonyloxy groups having 6 to 30 ring carbon atoms generally have the formula —C(=O)OR', wherein R' is a substituted or unsubstituted aromatic hydrocarbon group having 6 to 30 ring carbon atoms, wherein preferred aromatic hydrocarbon groups having 6 to 30 ring carbon atoms are mentioned above.

Examples of suitable boron-containing groups generally have one of the following formulae —B(OR')$_2$,

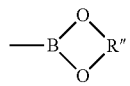

or —BR'$_2$, wherein the residues R' may be identical or different and are independently of each other a substituted or unsubstituted alkyl group having 1 to 30 carbon atoms or a substituted or unsubstituted aromatic hydrocarbon group having 6 to 30 ring carbon atoms; and R" is an alkylene group (i.e. alkane-diyl group) having 1 to 30 carbon atoms or a divalent aromatic hydrocarbon group having 6 to 30 ring carbon atoms, wherein preferred alkylene groups and preferred divalent aromatic hydrocarbon groups are mentioned above, preferably, R" is a C1-C3 alkylene group, wherein the alkylene chain may be substituted or unsubstituted by one or more of the substituents mentioned below.

Examples of the optional substituent(s) indicated by "substituted or unsubstituted" and "may be substituted" referred to above or hereinafter include a halogen atom (fluorine, chlorine, bromine, iodine), a cyano group, an alkyl group having 1 to 30, preferably 1 to 6 carbon atoms, a cycloalkyl group having 3 to 20, preferably 5 to 12 carbon atoms, an alkoxyl group having 1 to 20, preferably 1 to 5 carbon atoms, a haloalkyl group having 1 to 20, preferably 1 to 5 carbon atoms, a haloalkoxyl group having 1 to 20, preferably 1 to 5 carbon atoms, a silyl group, an aromatic hydrocarbon group having 6 to 30 ring carbon atoms, preferably 6 to 18 ring carbon atoms, an aryloxy group having 6 to 30, preferably 6 to 18 ring carbon atoms, an aralkyl group having 7 to 24, preferably 7 to 20 carbon atoms, an alkylthio group having 1 to 20, preferably 1 to 5 carbon atoms, an arylthio group having 6 to 30, preferably 6 to 18 ring carbon atoms, aromatic hydrocarbon group having 6 to 30 ring carbon atoms, and a heterocyclic group having 5 to 30 ring atoms, preferably 5 to 18 ring atoms.

The optional substituent is preferably a fluorine atom, a cyano group, an alkyl group having 1 to 30 carbon atoms, an aromatic hydrocarbon group having 6 to 30 ring carbon atoms, preferably 6 to 18 ring carbon atoms, and an heterocyclic group having 5 to 30 ring atoms, preferably 5 to 18 ring atoms; more preferably a fluorine atom, a phenyl group, a naphthyl group, a biphenyl group, a terphenyl group, a phenanthryl group, a triphenylenyl group, a fluorenyl group, a spirobifluorenyl group, a fluoranthenyl group, a residue based on a dibenzofuran ring, a residue based on a carbazole ring, a residue based on a dibenzothiophene ring, and their derivatives, a methyl group, an ethyl group, an n-propyl group, an isopropyl group, an n-butyl group, an s-butyl group, an isobutyl group, a t-butyl group, a cyclopentyl group, and a cyclohexyl group.

The optional substituent mentioned above may be further substituted by one or more of the optional substituents mentioned above.

The number of the optional substituents depends on the group which is substituted by said substituent(s). Preferred are 1, 2, 3 or 4 optional substituents, more preferred are 1, 2 or 3 optional substituents, most preferred are 1 or 2 optional substituents. In a further preferred embodiment, the groups mentioned above are unsubstituted.

The "carbon number of a to b" in the expression of "substituted or unsubstituted X group having a to b carbon atoms" is the carbon number of the unsubstituted X group and does not include the carbon atom(s) of an optional substituent.

The hydrogen atom referred to herein includes isotopes different from neutron numbers, i.e., light hydrogen (protium), heavy hydrogen (deuterium) and tritium.

The group

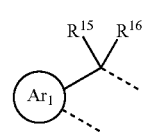

(II)

In the group

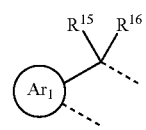

(II)

Ar$_1$ represents a substituted or unsubstituted aromatic hydrocarbon group having 6 to 30 ring carbon atoms or a substituted or unsubstituted heterocyclic group having 5 to 30 ring atoms, preferably a group of the following formula

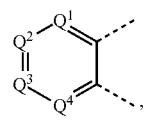

more preferably a group of the following formula

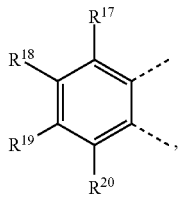

wherein
$Q^1$ is $CR^{11}$ or N; $Q^2$ is $CR^{12}$ or N; $Q^3$ is $CR^{13}$ or N and $Q^4$ is $CR^{14}$ or N;
$R^{11}$, $R^{12}$, $R^{13}$ and $R^{14}$ and $R^{17}$, $R^{18}$, $R^{19}$ and $R^{20}$
are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group; wherein
two or more substituents selected from $R^{11}$, $R^{12}$, $R^{13}$ and $R^{14}$ respectively selected from $R^{17}$, $R^{18}$, $R^{19}$ and $R^{20}$ may be bonded to each other to form a ring structure;
and
the dotted lines are bonding sites.
Most preferably, $Ar_1$ represents a group of formula

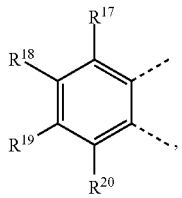

wherein
$R^{17}$, $R^{18}$, $R^{19}$ and $R^{20}$
are each independently hydrogen or a substituted or unsubstituted aromatic hydrocarbon group having 6 to 30 ring carbon atoms, a substituted or unsubstituted heterocyclic group having 5 to 30 ring atoms or a di-substituted amino group, wherein
two or more substituents selected from $R^{17}$, $R^{18}$, $R^{19}$ and $R^{20}$ may be bonded to each other to
form a ring structure, wherein the following ring structure is preferred:

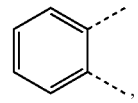

wherein the dotted lines are bonding sites;
preferably hydrogen, a substituted or unsubstituted aromatic hydrocarbon group having 6 to 30 ring carbon atoms, a substituted or unsubstituted heterocyclic group having 5 to 30 ring atoms or a di-substituted amino group.
Further most preferably, $Ar_1$ is

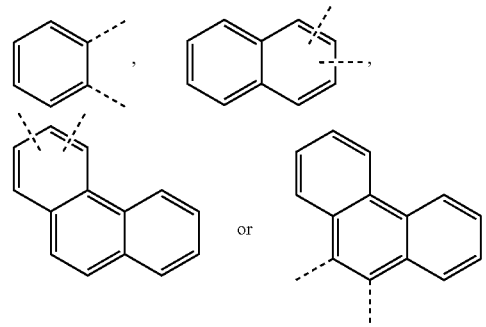

wherein the dotted lines are bonding sites.
$R^{15}$ and $R^{16}$
are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group; or $R^{15}$ and $R^{16}$ may be bonded to each other to form a ring structure;

preferably, $R^{15}$ and $R^{16}$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted aromatic hydrocarbon group having 6 to 30 ring carbon atoms; a substituted or unsubstituted heterocyclic group having 5 to 30 ring atoms; or a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; or $R^{15}$ and $R^{16}$ may be bonded to each other to form a ring structure;

more preferably, $R^{15}$ and $R^{16}$ are each independently methyl, ethyl, n-propyl, iso-propyl or phenyl; or $R^{15}$ and $R^{16}$ may be bonded to each other to form the following ring structure:

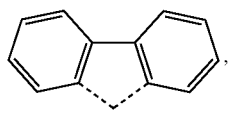

wherein the dotted lines are bonding sites.

Structure of the Compounds of Formula (I)

The compound of formula (1) preferably has one of the following structures:

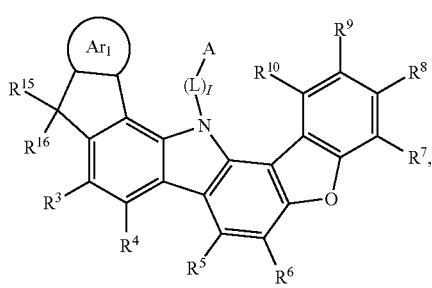
(Ia)

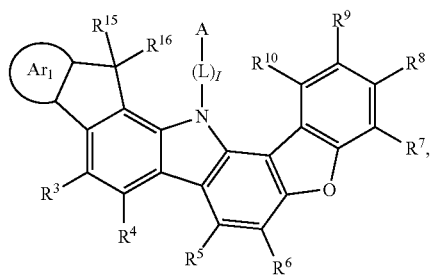
(Ib)

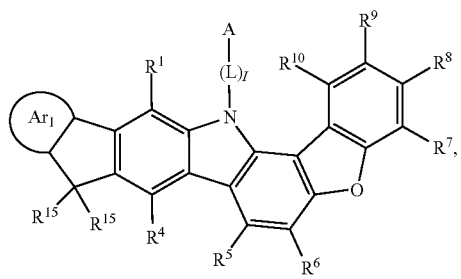
(Ic)

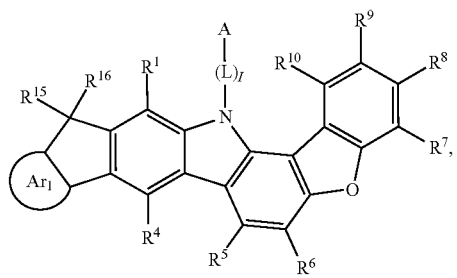
(Id)

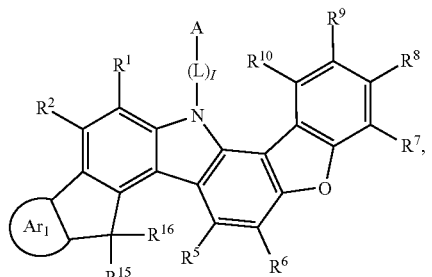
(Ie)

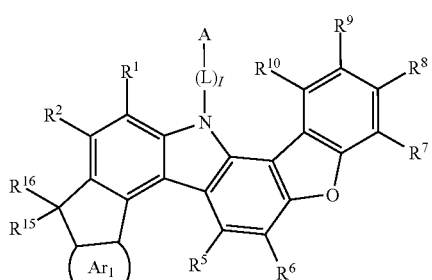
(If)

wherein
$R^1$, $R^2$, $R^3$ and $R^4$ are each independently hydrogen or $R^a$;
$Ar_1$ represents a substituted or unsubstituted aromatic hydrocarbon group having 6 to 30 ring carbon atoms or a substituted or unsubstituted heterocyclic group having 5 to 30 ring atoms, the dotted lines are bonding sites;
$R^5$, $R^6$, $R^7$, $R^8$, $R^9$, $R^{10}$, $R^{15}$, $R^{16}$ and $R^a$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

$R^{15}$ and $R^{16}$ may be bonded to each other to form a ring structure;

two or more substituents selected from $R^a$, $R^5$, $R^6$, $R^7$, $R^8$, $R^9$ and $R^{10}$ may be bonded to each other to form a ring structure;

A is a substituted or unsubstituted aromatic hydrocarbon group having 6 to 30 ring carbon atoms; or a substituted or unsubstituted heterocyclic group having 5 to 30 ring atoms.

L is a single bond, a substituted or unsubstituted alkylene group having 1 to 30 carbon atoms, a substituted or unsubstituted cycloalkylene group having 3 to 30 carbon atoms, a substituted divalent silyl group having 2 to 30 carbon atoms, a substituted or unsubstituted divalent aromatic hydrocarbon group having 6 to 30 ring carbon atoms, or a substituted or unsubstituted divalent heterocyclic group having 5 to 30 ring atoms;

l is 0, 1, 2 or 3.

Preferred symbols and indices in formulae (Ia), (Ib), (Ic), (Id), (Ie) and (If) are defined above and below.

Most preferred structures are structures (Ib), (Ic), (Id) and (Ie). Further most preferred is structure (Id).

More preferably, the compound of formula (1) preferably has one of the following structures:

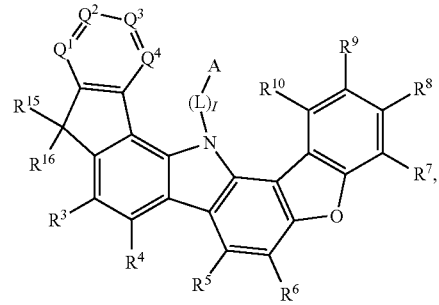
(Ia-1)

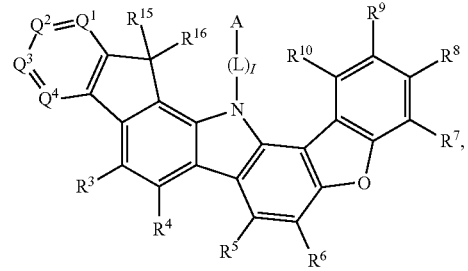
(Ib-1)

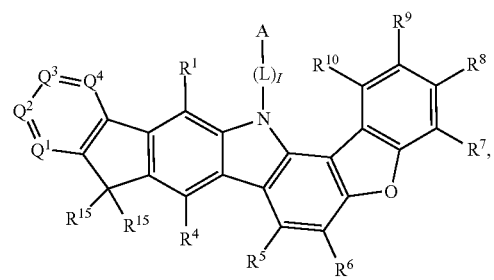
(Ic-1)

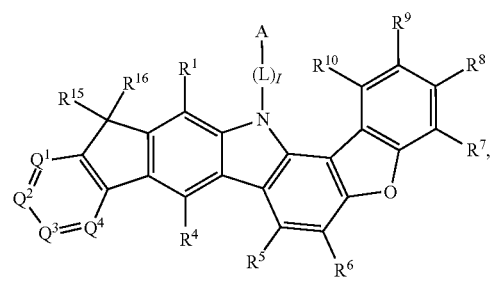
(Id-1)

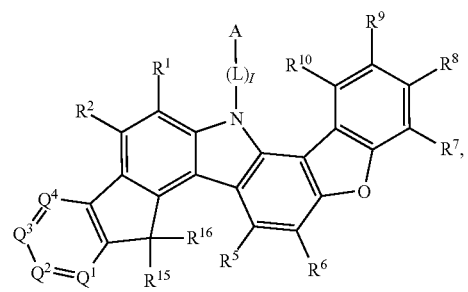
(Ie-1)

-continued

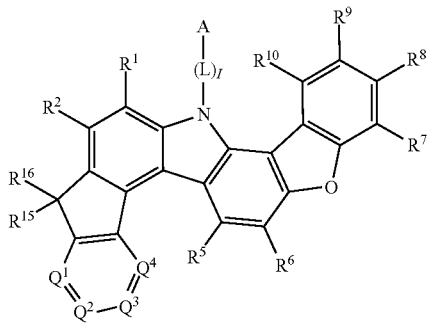

(If-1)

wherein $R^1$, $R^2$, $R^3$ and $R^4$ are each independently hydrogen or $R^a$;

$R^5$, $R^6$, R, $R^8$, $R^9$, $R^{10}$, $R^{15}$, $R^{16}$ and $R^a$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

$R^{15}$ and $R^{16}$ may be bonded to each other to form a ring structure;

two or more substituents selected from $R^a$, $R^5$, $R^6$, $R^7$, $R^8$, $R^9$ and $R^{10}$ may be bonded to each other to form a ring structure;

A is a substituted or unsubstituted aromatic hydrocarbon group having 6 to 30 ring carbon atoms; or a substituted or unsubstituted heterocyclic group having 5 to 30 ring atoms; $Q^1$ is $CR^{11}$ or N; $Q^2$ is $CR^{12}$ or N; $Q^3$ is $CR^{13}$ or N and $Q^4$ is $CR^{14}$ or N;

$R^{11}$, $R^{12}$, $R^{13}$ and $R^{14}$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms a substituted or unsubstituted aromatic hydrocarbon group having 6 to 30 ring carbon atoms; a substituted or unsubstituted aralkyl group having 7 to 31 ring carbon atoms; an amino group; a mono- or di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

two or more substituents selected from $R^{11}$, $R^{12}$, $R^{13}$ and $R^{14}$ may be bonded to each other to form a ring structure;

L is a single bond, a substituted or unsubstituted alkylene group having 1 to 30 carbon atoms, a substituted or unsubstituted cycloalkylene group having 3 to 30 carbon atoms, a substituted divalent silyl group having 2 to 30 carbon atoms, a substituted or unsubstituted divalent aromatic hydrocarbon group having 6 to 30 ring carbon atoms, or a substituted or unsubstituted divalent heterocyclic group having 5 to 30 ring atoms;

l is 0, 1, 2 or 3.

Preferred symbols and indices in formulae (Ia-1), (Ib-1), (Ic-1), (Id-1), (Ie-1) and (If-1) are defined above and below.

Most preferred structures are structures (Ib-1), (Ic-1), (Id-1) and (Ie-1). Further most preferred is structure (Id-1).

Most preferably, the compound of formula (I) has one of the following structures:

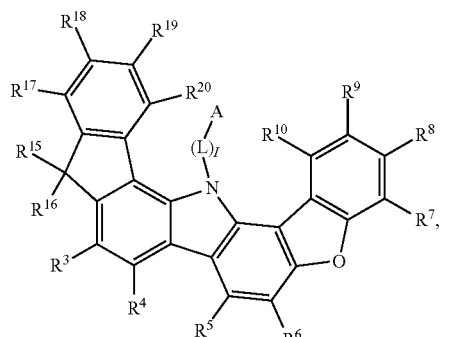
(Ia-1a)

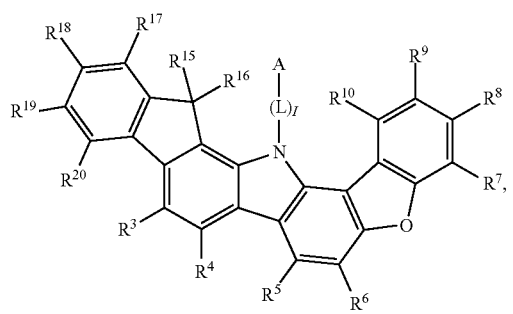
(Ib-1a)

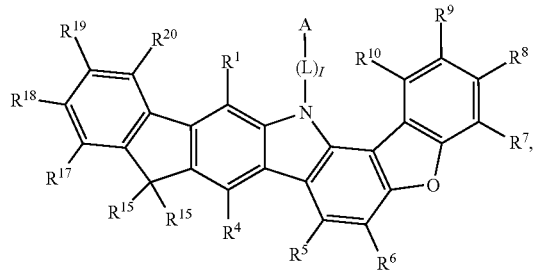
(Ic-1a)

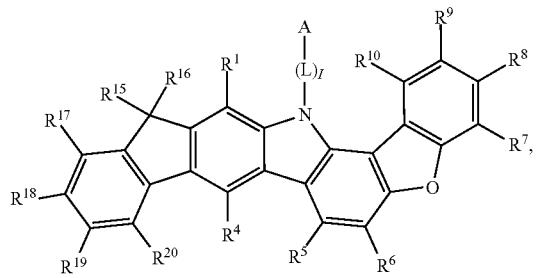
(Id-1a)

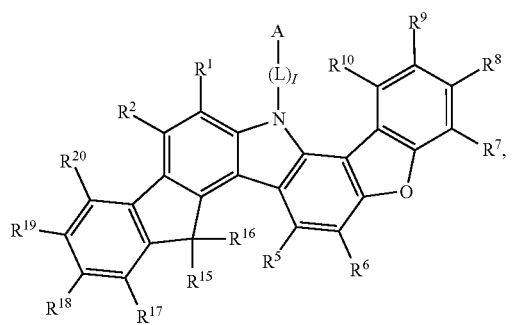
(Ie-1a)

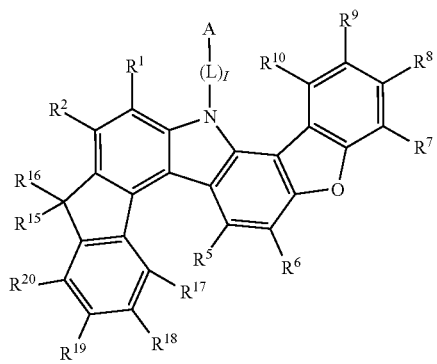
(If-1a)

wherein $R^1$, $R^2$, $R^3$ and $R^4$ are each independently hydrogen or $R^a$;

$R^5$, $R^6$, $R^7$, $R^8$, $R^9$, $R^{10}$, $R^{15}$, $R^{16}$ and $R^a$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

$R^{15}$ and $R^{16}$ may be bonded to each other to form a ring structure;

two or more substituents selected from $R^a$, $R^5$, $R^6$, $R^7$, $R^8$, $R^9$ and $R^{10}$ may be bonded to each other to form a ring structure;

A is a substituted or unsubstituted aromatic hydrocarbon group having 6 to 30 ring carbon atoms; or a substituted or unsubstituted heterocyclic group having 5 to 30 ring atoms;

$R^{17}$, $R^{18}$, $R^{19}$ and $R^{20}$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

two or more substituents selected from $R^{17}$, $R^{18}$, $R^{19}$ and $R^{20}$ may be bonded to each other to form a ring structure.

L is a single bond, a substituted or unsubstituted alkylene group having 1 to 30 carbon atoms, a substituted or unsubstituted cycloalkylene group having 3 to 30 carbon atoms, a substituted divalent silyl group having 2 to 30 carbon atoms, a substituted or unsubstituted divalent aromatic hydrocarbon group having 6 to 30 ring carbon atoms, or a substituted or unsubstituted divalent heterocyclic group having 5 to 30 ring atoms;

l is 0, 1, 2 or 3.

Preferred symbols and indices in formulae (Ia-1a), (Ib-1a), (Ic-1a), (Id-1a), (Ie-1a) and (If-1a) are defined above and below.

Most preferred structures are structures (Ib-1a), (Ic-1a), (Id-1a) and (Ie-1a): Further most preferred is structure (Id-1a).

$R^1$, $R^2$, $R^3$ and $R^4$, which are not Linked to One Another and Form a Group of Formula (II) and $R^5$, $R^6$, $R^7$, $R^8$, $R^9$, $R^{10}$ $R^1$, $R^2$, $R^3$ and $R^4$, which are not linked to one another and form a group of formula (II) are each independently hydrogen or $R^a$;

$R^5$, $R^6$, $R^7$, $R^8$, $R^9$, $R^{10}$ and $R^a$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

two or more substituents selected from $R^a$, $R^5$, $R^6$, $R^7$, $R^8$, $R^9$ and $R^{10}$ may be bonded to each other to form a ring structure.

Preferably, $R^1$, $R^2$, $R^3$ and $R^4$, which are not linked to one another and form a group of formula (II) are each independently hydrogen or $R^a$;

$R^5$, $R^6$, $R^7$, $R^8$, $R^9$, $R^{10}$ and $R^a$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted aromatic hydrocarbon group having 6 to 30 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted aryloxy group having 6 to 30 ring carbon atoms; a substituted or unsubstituted heterocyclic group having 5 to 30 ring atoms; a cyano group;

two or more substituents selected from $R^a$, $R^5$, $R^6$, $R^7$, $R^8$, $R^9$ and $R^{10}$ may be bonded to each other to form a ring structure.

More preferably, $R^1$, $R^2$ which are not linked to one another and form a group of formula (II) are hydrogen;

$R^3$ and $R^4$, which are not linked to one another and form a group of formula (II) are each independently hydrogen or $R^a$;

$R^9$ and $R^{10}$ are hydrogen;

$R^5$, $R^6$, $R^7$, $R^8$ and $R^a$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted aromatic hydrocarbon group having 6 to 30 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted aryloxy group having 6 to 30 ring carbon atoms; a substituted or unsubstituted heterocyclic group having 5 to 30 ring atoms; a cyano group;

two or more substituents selected from $R^a$, $R^5$, $R^6$, $R^7$, $R^8$, $R^9$ and $R^{10}$ may be bonded to each other to form a ring structure.

Most preferably, $R^1$, $R^2$ which are not linked to one another and form a group of formula (II) are hydrogen;

$R^3$ and $R^4$, which are not linked to one another and form a group of formula (II) are each independently hydrogen or $R^a$;

$R^9$ and $R^{10}$ are hydrogen;

$R^5$, $R^6$, $R^7$, $R^8$ and $R^a$ are each independently hydrogen, a substituted or unsubstituted alkyl group having 1 to 8 carbon atoms, preferably methyl group, ethyl group, n-propyl group, isopropyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a di-substituted amino group having substituents independently selected from the group consisting of a substituted or unsubstituted alkyl group having 1 to 8 carbon atoms, a substituted or unsubstituted aromatic hydrocarbon group having 6 to 18 ring carbon atoms and a substituted or unsubstituted heterocyclic group having 5 to 18 ring atoms, preferably di-substituted amino group having substituents selected from the group consisting of phenyl group, 1-naphthyl group, 2-naphthyl group, biphenyl-2-yl group, biphenyl-3-yl group, biphenyl-4-yl group, methyl group, ethyl group, n-propyl group, isopropyl group, n-butyl group, s-butyl group, isobutyl group, and t-butyl group; a substituted or unsubstituted alkoxy group having 1 to 8 carbon atoms, preferably methoxy group, ethoxy group, n-propyloxy group, isopropyloxy group, n-butyloxy group, s-butyloxy group, isobutyloxy group, t-butyloxy group; a substituted or unsubstituted heterocyclic group having 5 to 18 ring atoms, preferably triazine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; a cyano group;

two or more substituents selected from $R^5$, $R^6$, $R^7$, $R^8$, $R^3$ and $R^4$ may be bonded to each other to form a ring structure.

Preferred ring structures formed by two or more substituents $R^a$, $R^5$, $R^6$, $R^7$, $R^8$, $R^9$ and $R^{10}$, preferably $R^5$, $R^6$, $R^7$, $R^8$, $R^3$ and $R^4$ are selected from the group consisting of:

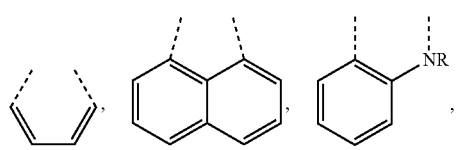

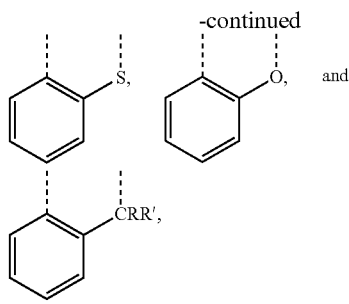

wherein R and R' are each independently a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms, and the dotted lines are bonding sites.

The group $-(L)_l-A$

L represents a single bond, a substituted or unsubstituted alkylene group having 1 to 30 carbon atoms, a substituted or unsubstituted cycloalkylene group having 3 to 30 carbon atoms, a substituted divalent silyl group having 2 to 30 carbon atoms, a substituted or unsubstituted divalent aromatic hydrocarbon group having 6 to 30 ring carbon atoms, or a substituted or unsubstituted divalent heterocyclic group having 5 to 30 ring atoms;

more preferably, L is a single bond, 1,3-phenylene, 1,4-phenylene, 1,2-phenylene, 5-phenyl-1,3-phenylene, biphenylene, divalent dibenzofuran or divalent dibenzothiophene;

most preferably, L is 1,3-phenylene, 1,4-phenylene or a single bond;

further most preferably, L is 1,3-phenylene or a single bond.

l is 0, 1, 2 or 3; in the case that l is 2 or 3, L is the same or different in each occurrence, preferably l is 1.

A is a substituted or unsubstituted aromatic hydrocarbon group having 6 to 30 ring carbon atoms; or a substituted or unsubstituted heterocyclic group having 5 to 30 ring atoms; or a disubstituted amino group.

In one preferred embodiment, A is represented by formula (III)

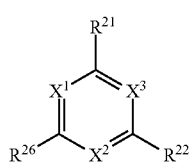

(III)

wherein $X^1$, $X^2$ and $X^3$ each independently represent $CR^{23}$ or an N atom, wherein each $R^{23}$ may be the same or different, preferably at least one of $X^1$, $X^2$ and $X^3$ is N;

$R^{21}$, $R^{22}$, $R^{23}$ and $R^{26}$ each independently represent hydrogen, a halogen atom, a substituted or unsubstituted alkyl group having 1 to 30 carbon atoms, a substituted or unsubstituted alkenyl group having 2 to 31 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, preferably, $R^{21}$, $R^{22}$, $R^{23}$ and $R^{26}$ each independently represent hydrogen, a substituted or unsubstituted alkyl group having 1 to 30 carbon atoms, a substituted or unsubstituted aromatic hydrocarbon group having 6 to 30 ring carbon atoms, a substituted or unsubstituted heterocyclic group having 5 to 30 ring atoms, or a cyano group, more preferably, $R^{21}$, $R^{22}$, $R^{23}$ and $R^{26}$ each independently represent hydrogen, a substituted or unsubstituted alkyl group having 1 to 8 carbon atoms, preferably methyl group, ethyl group, n-propyl group, iso-propyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a substituted or unsubstituted heterocyclic group having 5 to 18 ring atoms, preferably triazine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; or a cyano group;

provided that, among $R^{21}$, $R^{22}$, $R^{26}$ and $R^{23}$, if $X^1$, $X^2$ and/or $X^3$ are $CR^{23}$, any two of $R^{21}$, $R^{22}$, $R^{23}$ and $R^{26}$ may be bonded each other to form ring structures;

wherein one of $R^{21}$, $R^{22}$, $R^{26}$ and, if $X^1$, $X^2$ and/or $X^3$ are $CR^{23}$, $R^{23}$, represents a bonding site to $-(L)_l-$.

Preferred groups of formula (III) are selected from (IIIa), (IIIb), (IIIc), (IIId), (IIIe), and (IIIf).

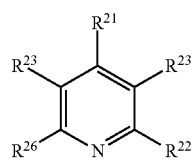

(IIIa)

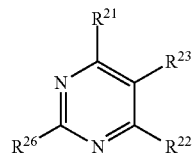

(IIIb)

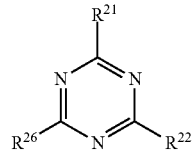

(IIIc)

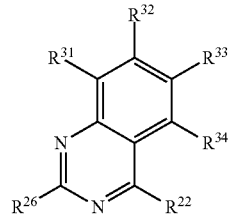

(IIId)

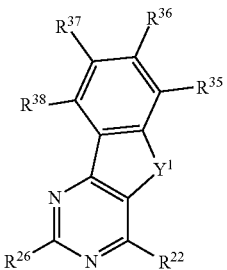

(IIIe)

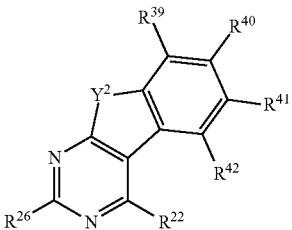

(IIIf)

wherein $Y^1$ and $Y^2$ each independently represent O, S, $NR^{43}$ or $CR^{44}R^{45}$, preferably S, $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ each independently represent hydrogen, a halogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, preferably, $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ each independently represent hydrogen, a substituted or unsubstituted alkyl group having 1 to 30 carbon atoms, a substituted or unsubstituted aromatic hydrocarbon group having 6 to 30 ring carbon atoms, a substituted or unsubstituted heterocyclic group having 5 to 30 ring atoms, or a cyano group, more preferably, $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ each independently represent hydrogen, a substituted or unsubstituted alkyl group having 1 to 8 carbon atoms, preferably methyl group, ethyl group, n-propyl group, iso-propyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a substituted or unsubstituted heterocyclic group having 5 to 18 ring atoms, preferably triazine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; or a cyano group;

provided that, among from $R^{21}$, $R^{22}$, $R^{23}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$, any two of from $R^{21}$, $R^{22}$, $R^{23}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ may be bonded each other to form ring structures;

wherein one of $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ represents a bonding site to -(L)$_l$-.

Examples for preferred groups of formula (III) are:

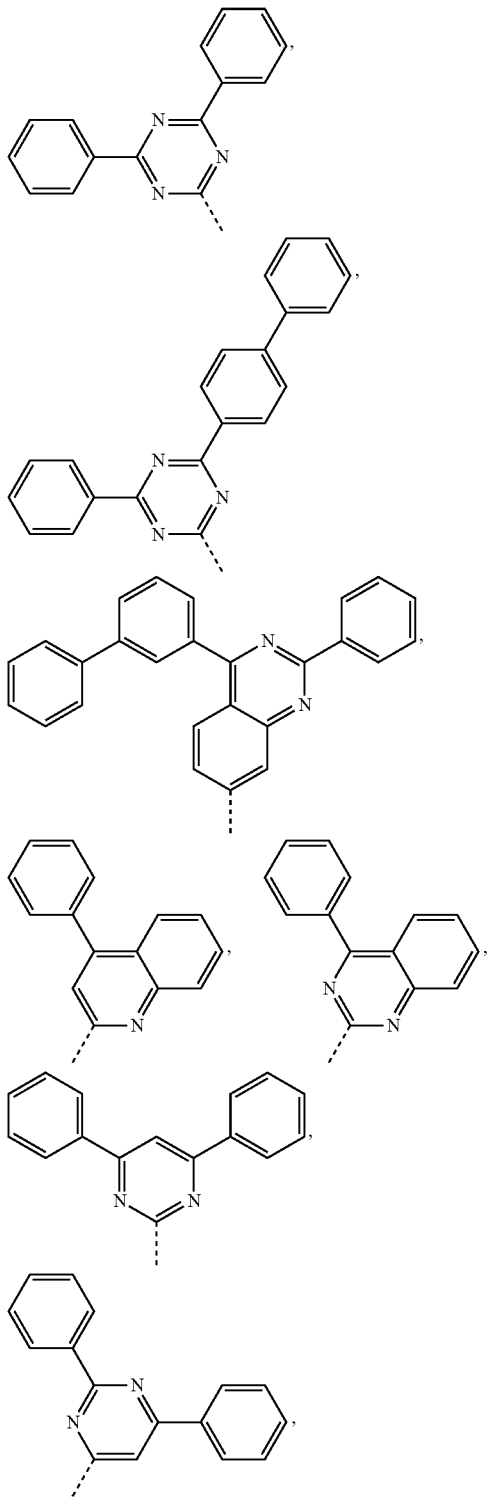

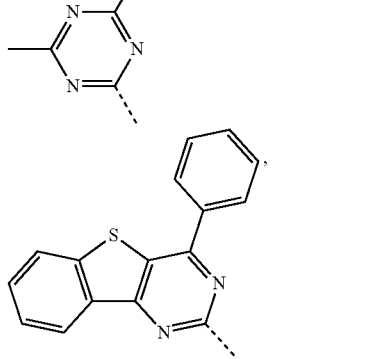

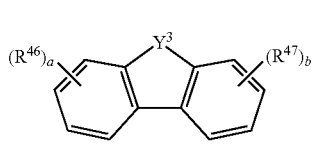

wherein the dotted lines are bonding sites.

In a further embodiment, A is represented by formula (IVa)

$$(R^{46})_a \text{―} \overset{Y^3}{\underset{}{\text{○○}}} \text{―} (R^{47})_b \quad \text{(IVa)}$$

wherein $Y^3$ represents O, S or $NR^{48}$, preferably O or S, $R^{46}$, $R^{47}$ and $R^{48}$ each independently represent a halogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, preferably, $R^{46}$, $R^{47}$ and $R^{48}$ each independently represent a substituted or unsubstituted alkyl group having 1 to 30 carbon atoms, a substituted or unsubstituted aromatic hydrocarbon group having 6 to 30 ring carbon atoms, a substituted or unsubstituted heterocyclic group having 5 to 30 ring atoms, or a cyano group, more preferably, $R^{46}$, $R^{47}$ and $R^{48}$ each independently represent a substituted or unsubstituted alkyl group having 1 to 8 carbon atoms, preferably methyl group, ethyl group, n-propyl group, isopropyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a substituted or unsubstituted heterocyclic group having 5 to 18 ring atoms, preferably triazine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; or a cyano group;

a is 0, 1, 2, 3 or 4, preferably 0, 1 or 2, more preferably 0;

b is 0, 1, 2, 3 or 4, preferably 0, 1 or 2, more preferably 0;

when a is more than 1, the $R^{46}$s may be the same or different and are allowed to be bonded to each other to form a ring structure, when b is more than 1, the $R^{47}$s may be the same or different and are allowed to be bonded to each other to form a ring structure, wherein one of $R^{46}$, $R^{47}$ and $R^{48}$ represents a bonding site to -(L)$_l$-.

Examples of preferred groups of formula (IVa) are:

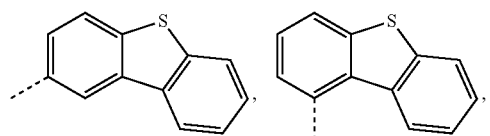

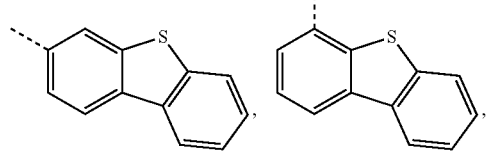

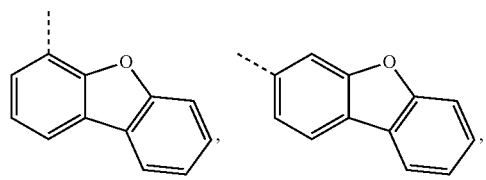

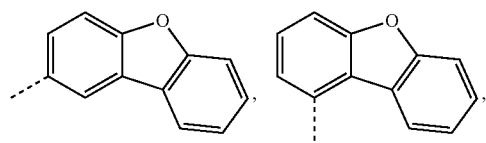

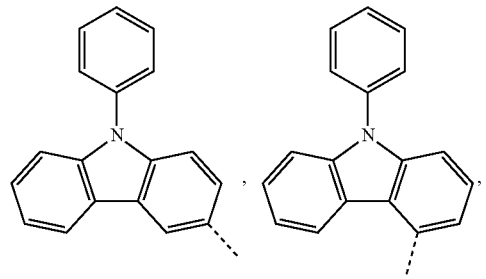

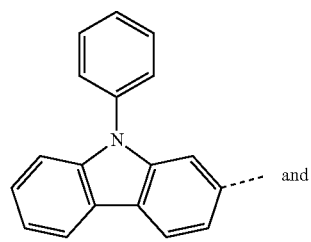 and

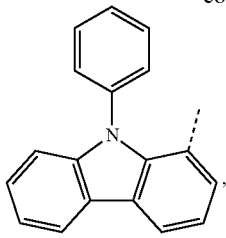

wherein the dotted lines are bonding sites.

In a further embodiment, A represents a substituted or unsubstituted aromatic hydrocarbon group having 6 to 30 ring carbon atoms, preferably, A represents a substituted or unsubstituted aromatic hydrocarbon group having 6 to 18 ring carbon atoms, more preferably phenyl, naphthyl, phenanthryl, triphenylenyl, fluorenyl and fluoranthenyl, most preferably, A represents phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group.

Suitable disubstituted amino groups are for example represented by formula —NR$^a$R$^b$, wherein R$^a$ and R$^b$ are each independently a substituted or unsubstituted aromatic hydrocarbon group having 6 to 30 ring carbon atoms, a substituted or unsubstituted heterocyclic group having 5 to 30 ring atoms, preferably a substituted or unsubstituted aromatic hydrocarbon group having 6 to 18 ring carbon atoms or a substituted or unsubstituted heterocyclic group having 5 to 18 ring atoms, more preferably a substituted or unsubstituted aromatic hydrocarbon group having 6 to 18 ring carbon atoms, most preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; for example:

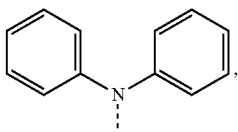

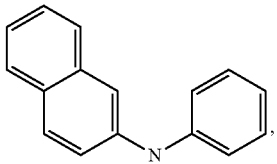

wherein the dotted lines are bonding sites.

Examples for Most Preferred Compounds of Formula (I)

Suitable and preferred compounds of formula (I) are mentioned above. Examples for compounds of formula (I) are compounds of formula (Ia), (Ib), (Ic), (Id), (Ie) or (If). Suitable and preferred residues $R^1$, $R^2$, $R^3$ and $R^4$, which are not linked to one another and form a group of formula (II), $R^5$, $R^6$, $R^7$, $R^8$, $R^9$, $R^{10}$, $R^a$, $R^{15}$, $R^{16}$, $R^{17}$, $R^{18}$, $R^{19}$, $R^{20}$ and groups Ar$_1$, Q$^1$, Q$^2$, Q$^3$ and Q$^4$ are defined above.

Examples of compounds of formula (1) are mentioned below:
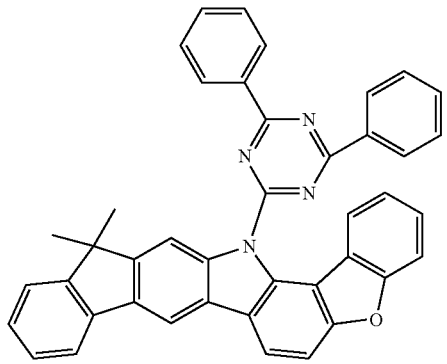
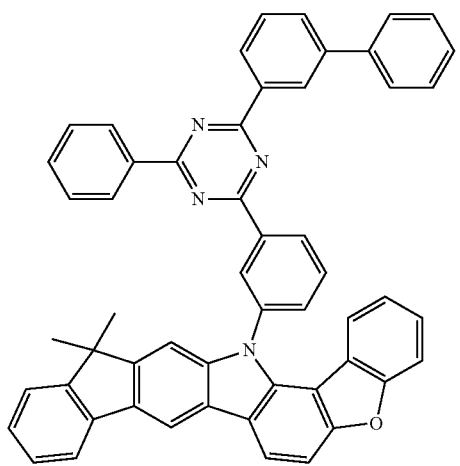
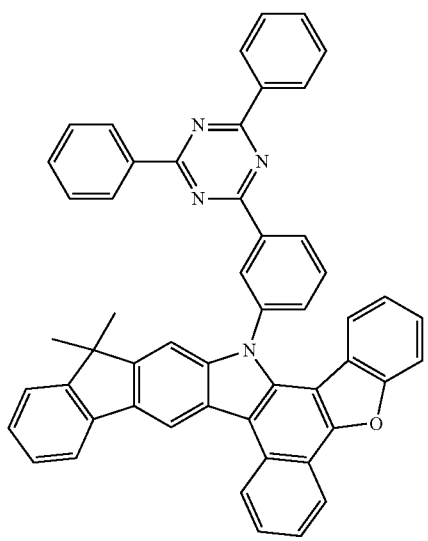
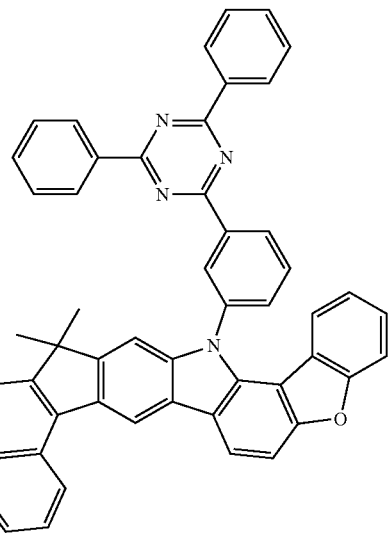
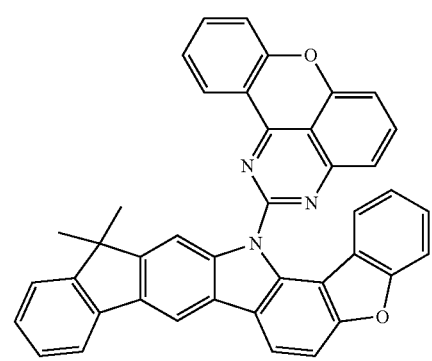
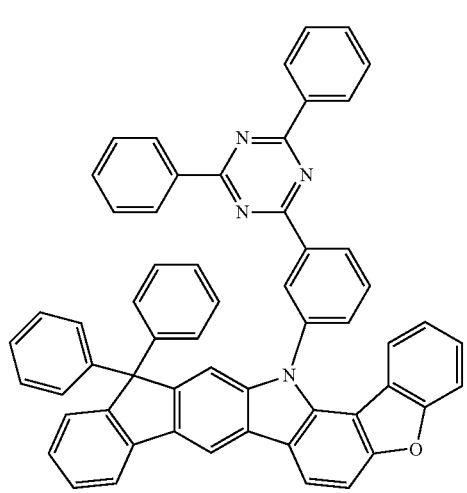

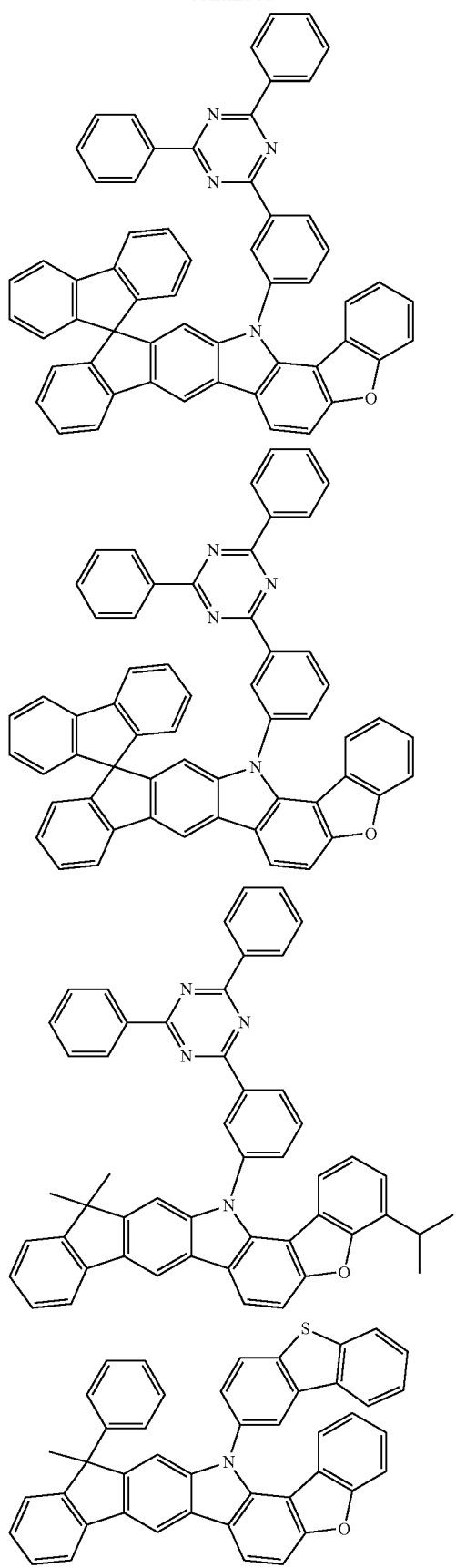
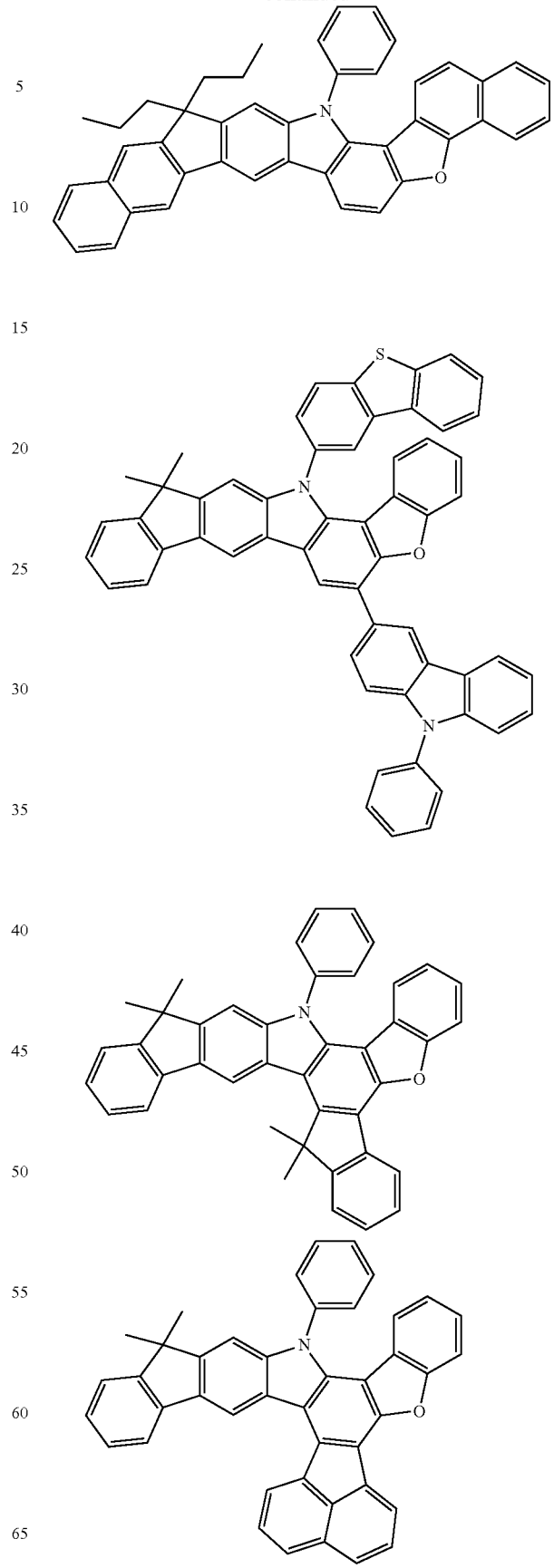

37
-continued
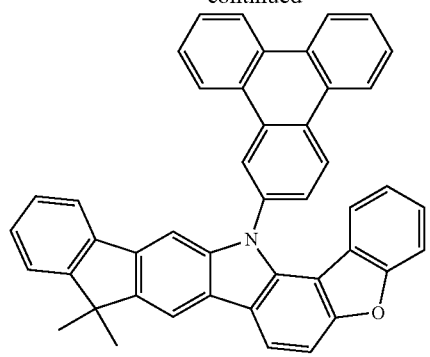
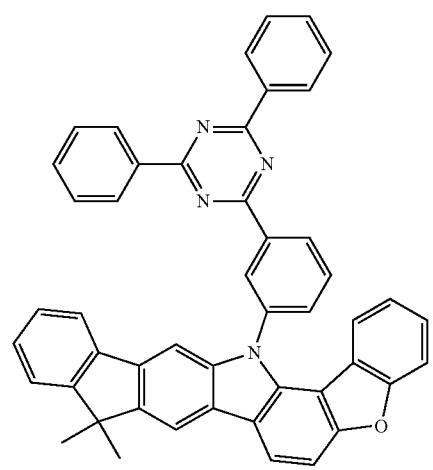
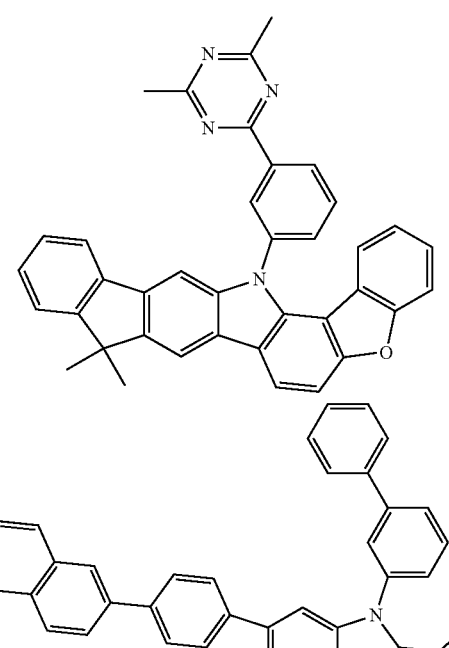
38
-continued
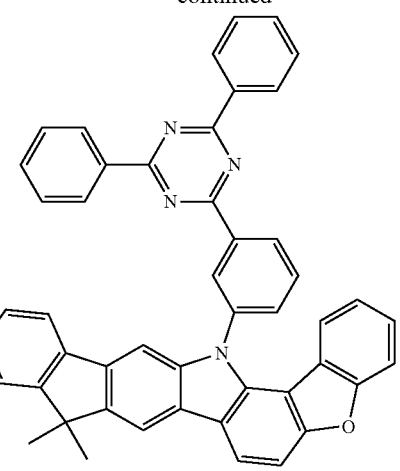
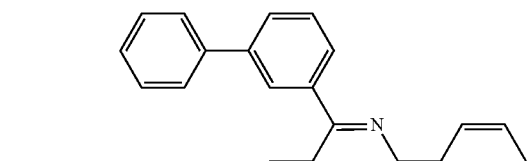
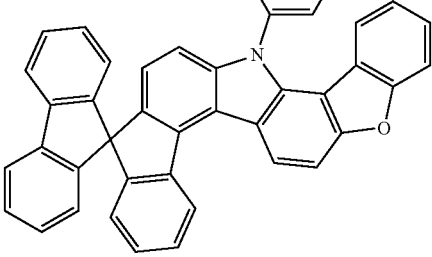
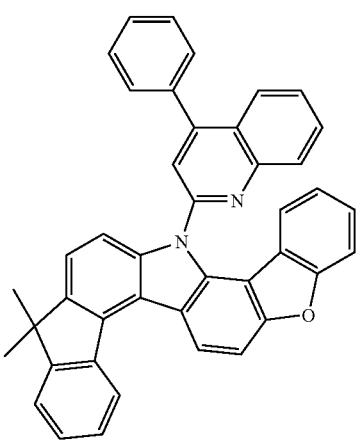

39
-continued
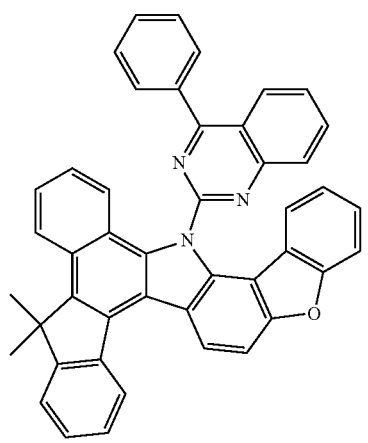
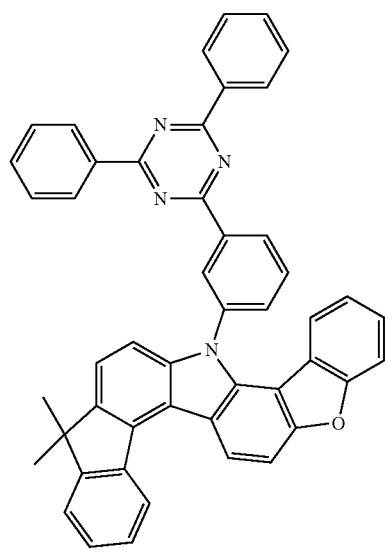
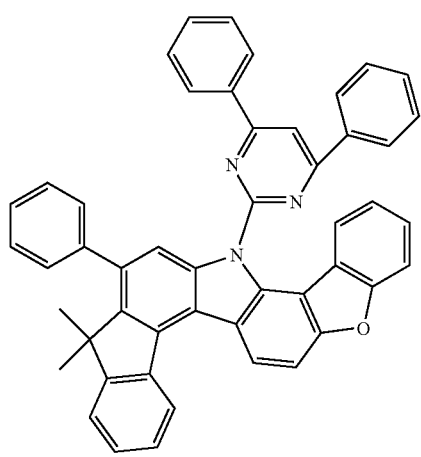
40
-continued
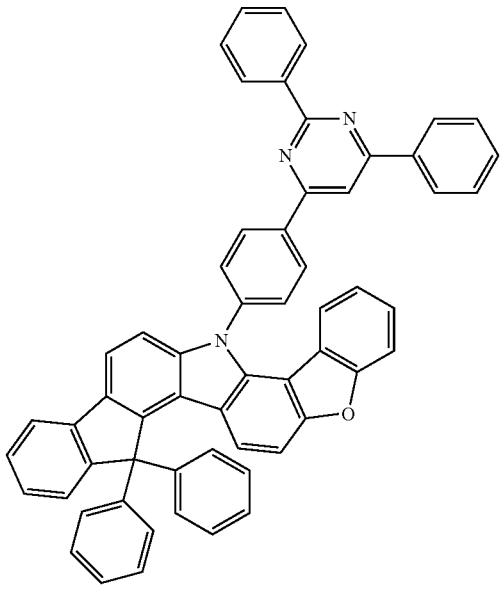
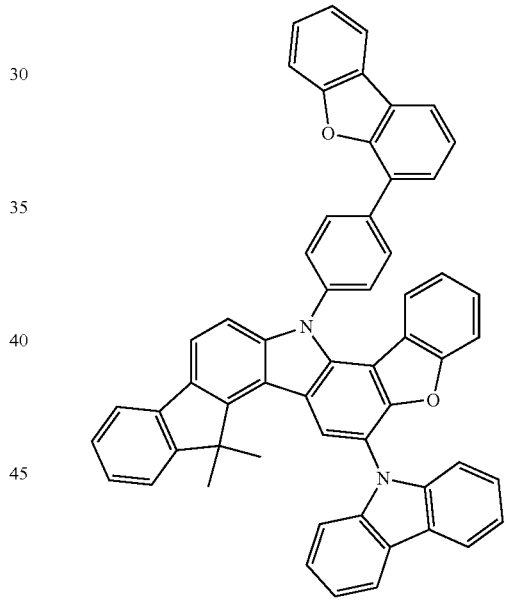
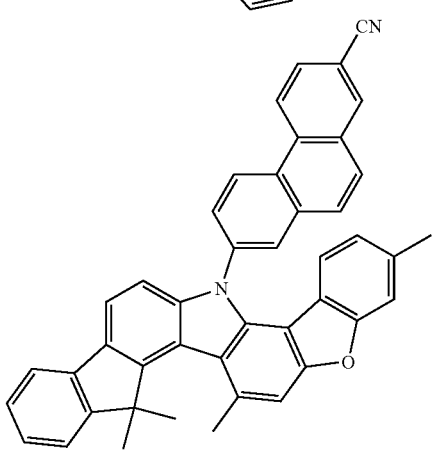

41
-continued
42
-continued
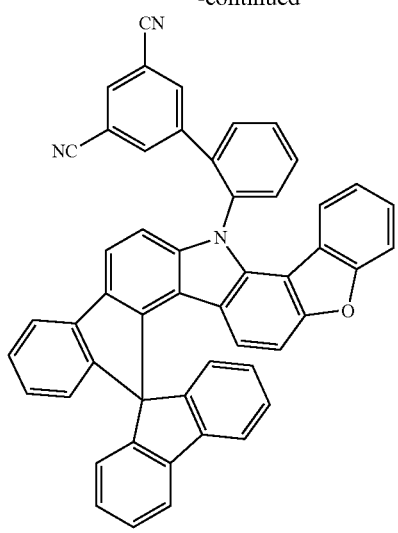
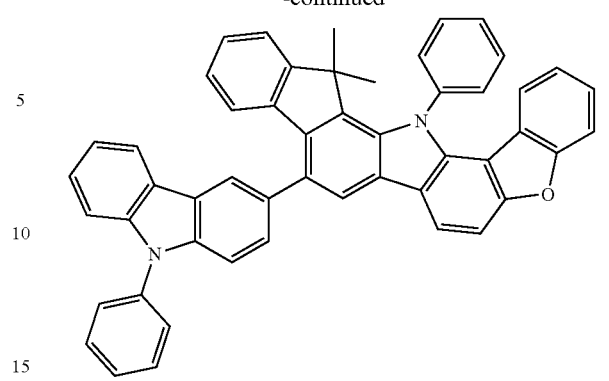
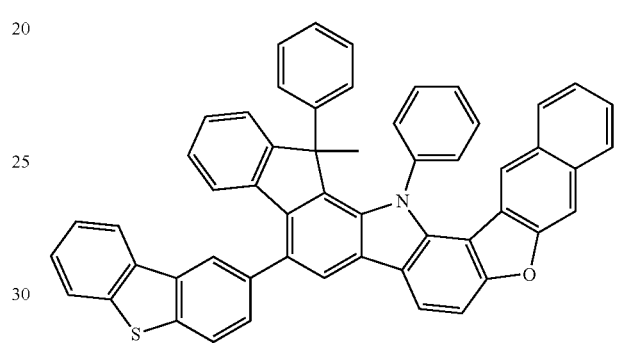
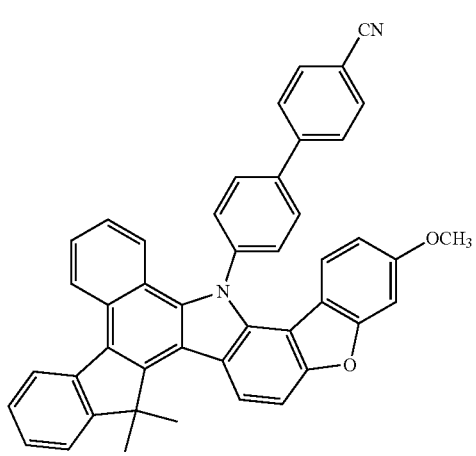
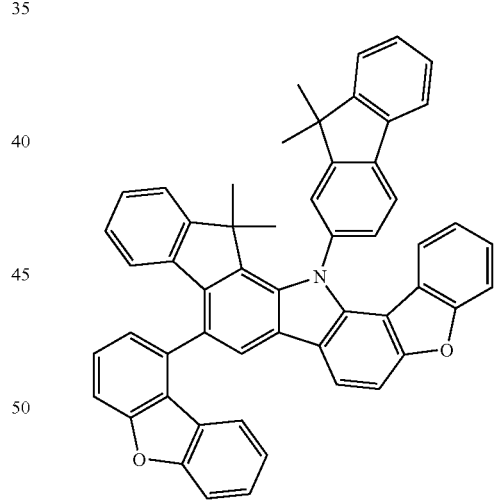
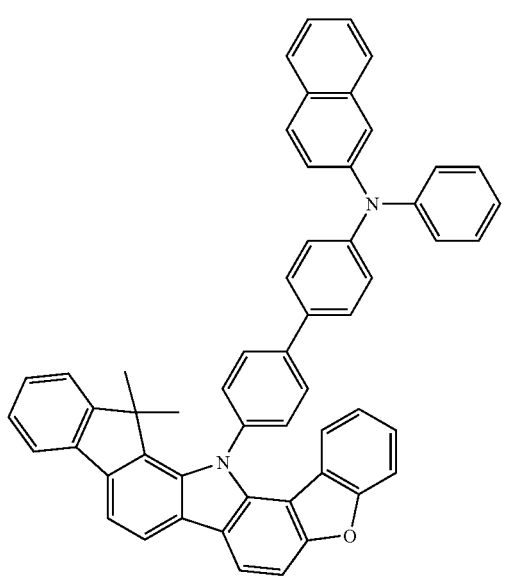

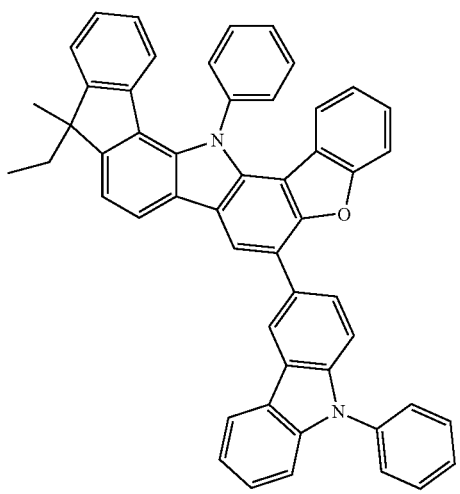
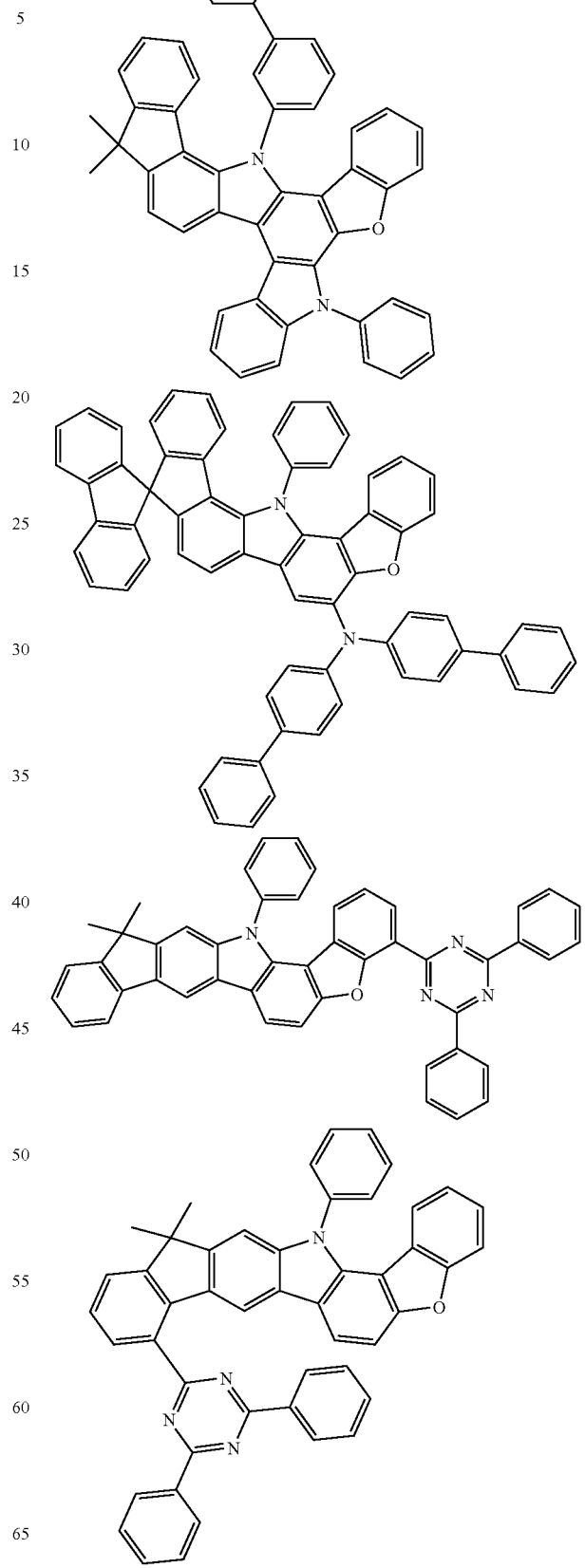

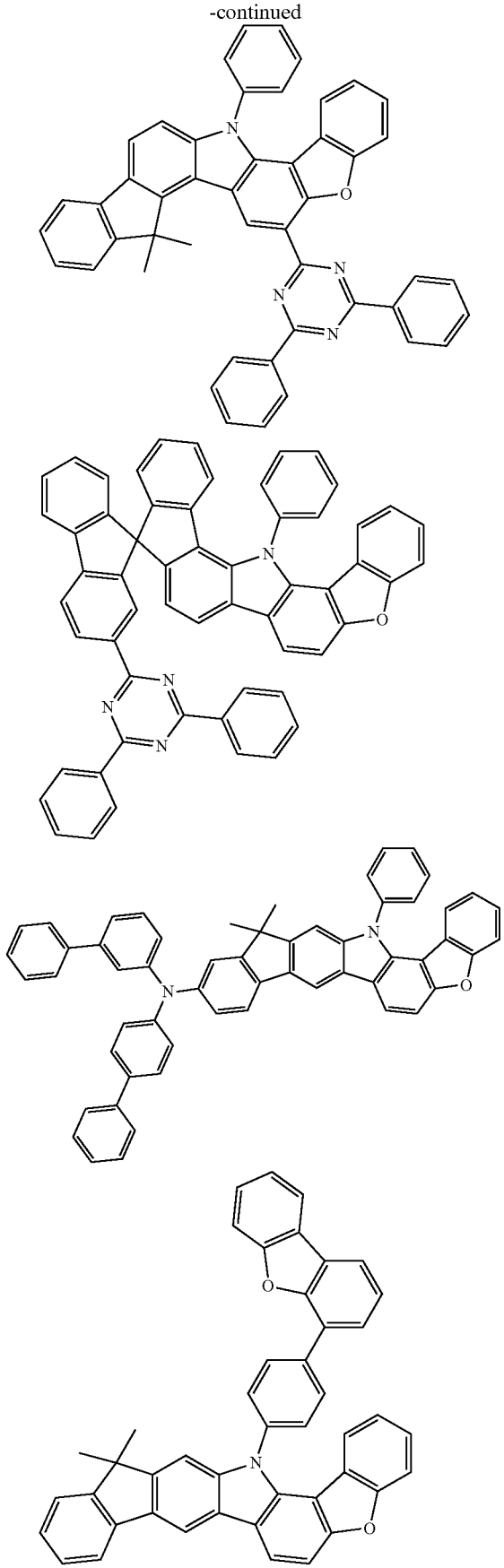
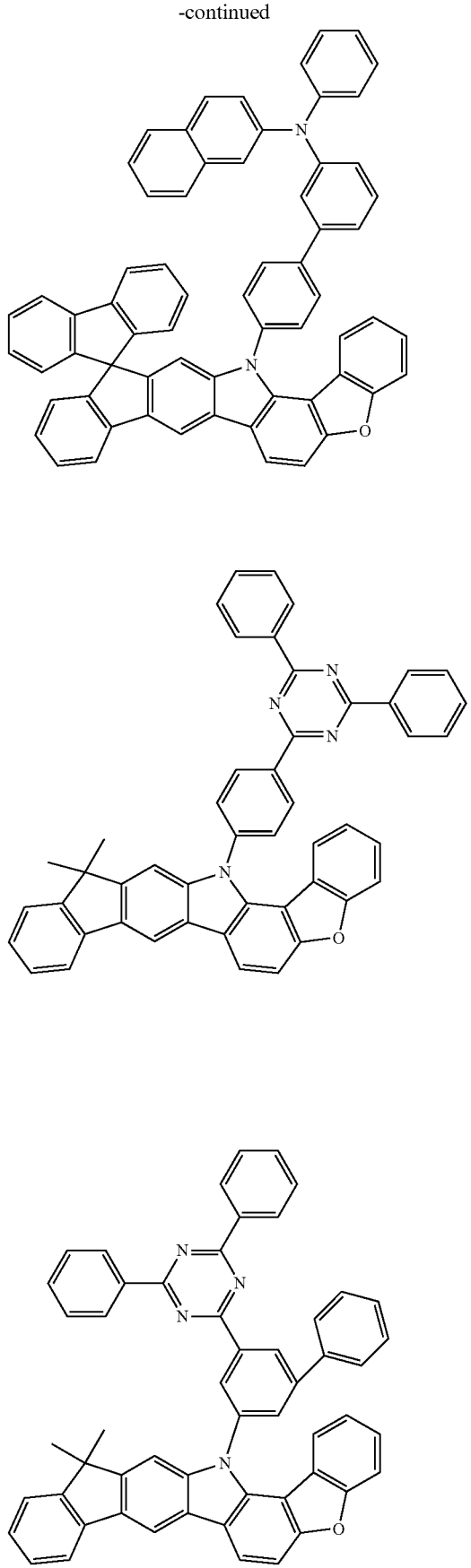

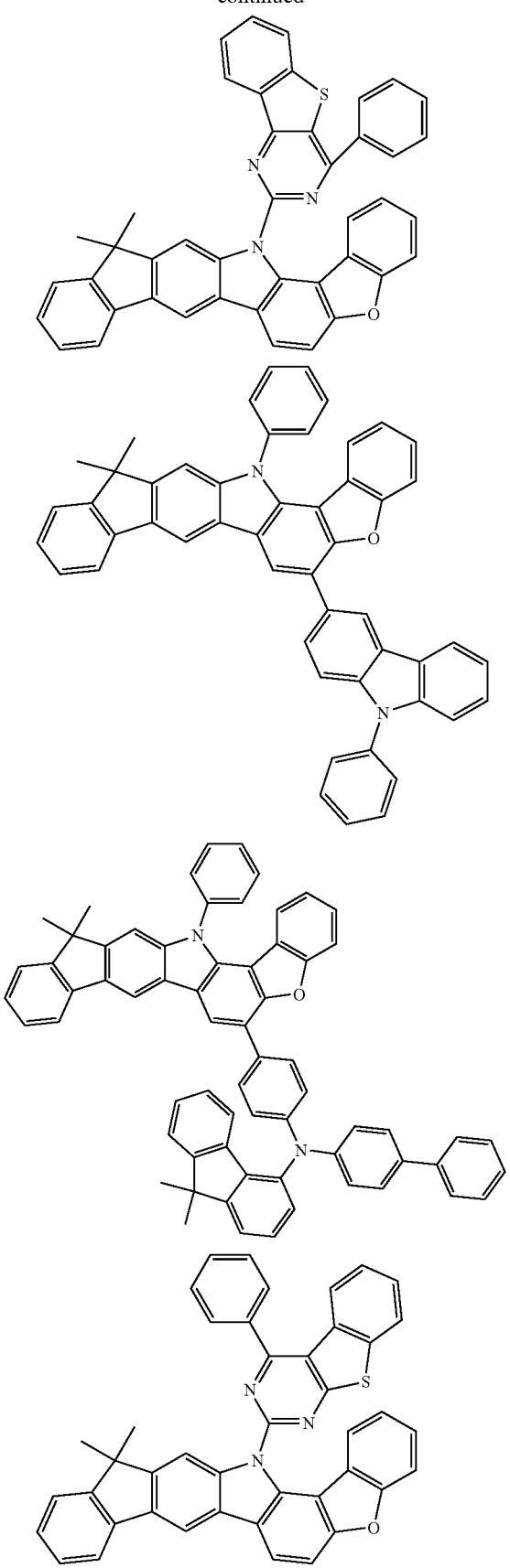
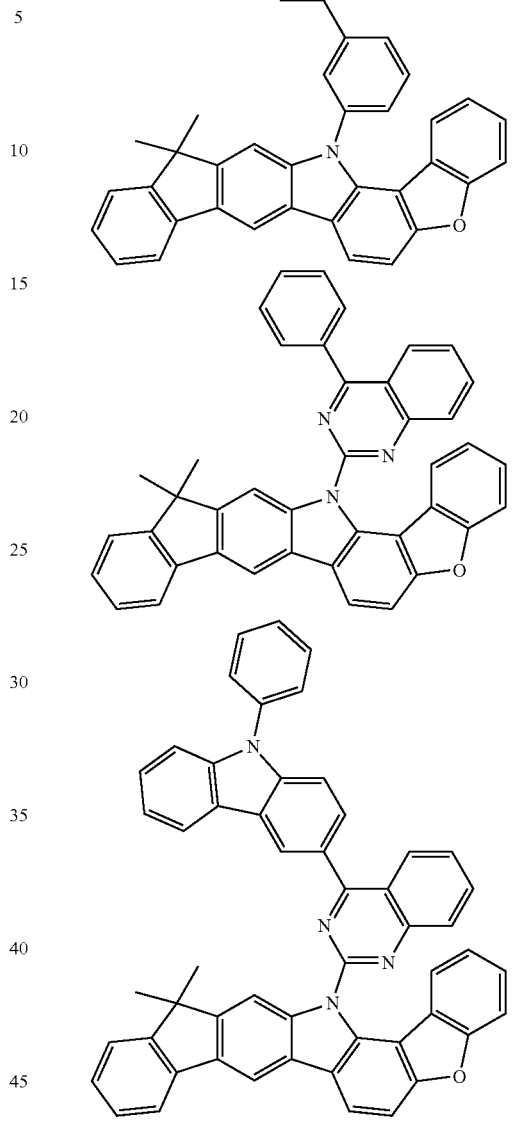
Synthesis of the Compounds of Formula (1)
The compounds of formula (I) are for example prepared as shown in the following, wherein the preparation of the compound of formula (a) is shown:
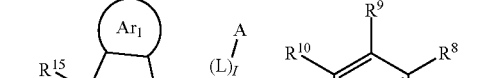

Step (i)

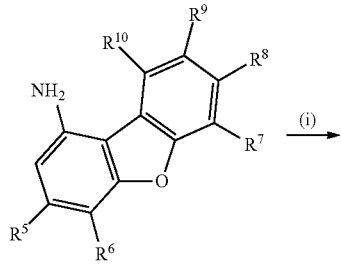

Step (ii)

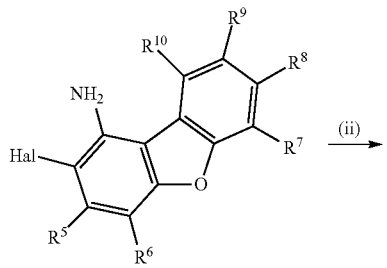

Step (iii)

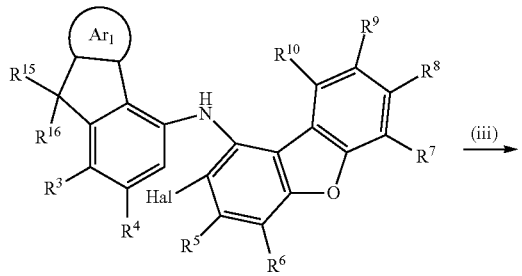

-continued

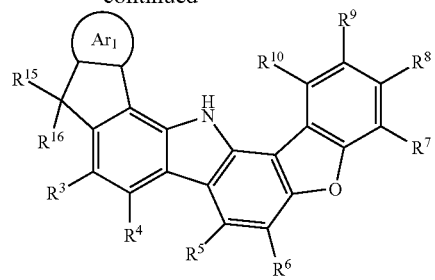

Step (iv)

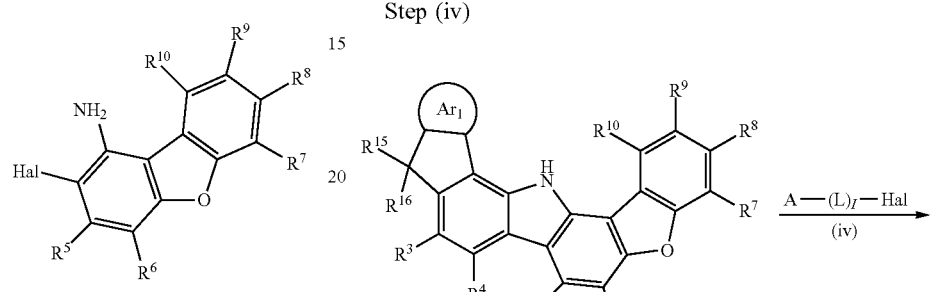

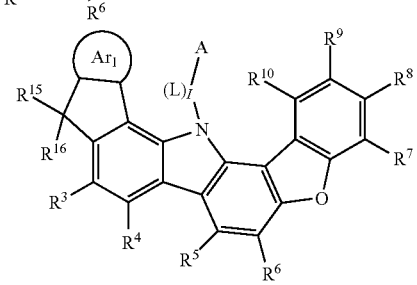

The compounds of formulae (Ib), (Ic), (Id), (Ie) and (If) are prepared analogously Step (i)

In step (i) a halogenation is carried out, generally as known in the art, for example a halogenation with N-chlorosuccinimide in $CCl_4$ as a solvent at 90° C. for 2h.

Step (ii)

In step (ii) a substitution of the —NH₂ group with

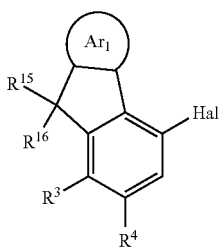

(wherein Hal is F, Cl, Br or I, preferably Br) is carried out, wherein suitable process parameters are generally known in the art. For example in the presence of Pd(II)acetate and NaOiBu and (±)-2,2'-bis(diphenylphosphino)-1,1'-binaphthalene in Xylene as a solvent at 145° C. for 5h.

Step (iii)

In step (iii) a cyclization is carried out, wherein suitable process parameters are generally known in the art. For example in the presence of Pd(II)acetate, tricyclohexylphosphinetetrafluoroborate and K$_2$CO$_3$ in N,N-dimethylacetamide as a solvent at 145° C. for 22h.

Step (iv)

In step (iv) a substitution of the —NH— group with A-(L)$_r$-Hal (wherein Hal is F, Cl, Br or I, preferably Br) is carried out, wherein suitable process parameters are generally known in the art. For example in the presence of tris(benzylideneacetone)di-Pd(0), 4,5-bis(diphenyl-phosphino)-9,9-dimethylxanthene and NaO$^t$Bu in xylene as a solvent at 145° C. for 3h.

Details of the reaction step and process conditions are mentioned above and in the examples of the present application.

Compounds of Formula (I) in Organic Electronics Applications

It has been found that the compounds of the formula (1) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The term organic EL device (organic electroluminescence device) is used interchangeable with the term organic light-emitting diode (OLED) in the following; i.e. both terms have the same meaning in the sense of the present application.

The present invention further relates to a material for an organic EL device comprising at least one compound of formula (1).

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula (1).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes.

When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with β-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula (I).

The compounds of formula (I) being particularly suitable in OLEDs for use as matrix material (host material) in a light-emitting layer and/or as charge and/or exciton blocker material, i.e. as electron/exciton blocker material or as hole/exciton blocker material, and/or charge transport material, i.e. hole transport material or electron transport material, preferably as matrix material in a light-emitting layer and/or as electron transport material, especially in combination with a phosphorescence emitter.

In the case of use of the inventive compounds of formula (I) in OLEDs, OLEDs which have long lifetimes and which can be operated especially at low use and operating voltage are obtained.

The inventive compounds of formula (I) are suitable especially for use as matrix and/or charge transport, i.e. hole or electron transport, and/or charge blocker material, i.e. hole or electron blocker material. Furthermore, the compounds of the formula (I) can be used as conductor/complementary materials in organic electronics applications selected from switching elements and organic solar cells. (In the sense of the present application, the terms matrix and host are used interchangeable).

Organic EL Device (OLED)

The organic EL device as one embodiment of the invention comprises one or more organic thin film layers including an emitting layer between a cathode and an anode, and at least one layer of the organic thin film layers comprises the compound of formula (I).

As examples of the organic thin film layers that comprise the compound of formula (I), an anode-side organic thin film layer (hole-transporting layer, hole-injecting layer, or the like), an emitting layer, a cathode-side organic thin film layer (electron-transporting layer, electron-injecting layer, or the like) provided between a cathode and an emitting layer, a spacing layer, a barrier layer or the like can be given. The examples are not limited thereto.

The compound of formula (I) may be contained in any of the abovementioned layers, and can be used as a host material or a dopant material in the emitting layer of a fluorescent emitting unit, a host material in the emitting layer of a phosphorescent emitting unit, a hole-transporting layer, an electron-transporting layer or the like of an emitting unit.

Preferably, the compounds of the formula (I) are used as matrix materials (host materials), preferably in an emitting layer of an OLED, more preferably in an emitting layer of an OLED comprising at least one compound of the formula (I) and at least one emitter material, wherein the emitter material is preferably a fluorescent or phosphorescent emitter material, more preferably a green or red fluorescent or phosphorescent emitter material.

According to the other embodiment, the compounds of the formula (I) are preferably used as electron transporting layer of an OLED.

The organic EL device of the invention may be a fluorescent or phosphorescent monochromatic emitting device or may be a fluorescent/phosphorescent hybrid white emitting device. It may be a simple emitting device having a single emitting unit or a tandem emitting device having plural emitting units. Among them, the organic EL device may preferably be a phosphorescent emitting device.

As the representative device structure of a simple type organic EL device, the following device configuration can be given.

(1) Anode/Emitting Unit/Cathode

The emitting unit mentioned above may be a stacked type emitting unit comprising plural phosphorescent emitting layers or plural fluorescent emitting layers. In this case, in order to prevent diffusion of excitons generated in the phosphorescent emitting layer to the fluorescent emitting layer, a spacing layer may be provided between the emitting layers. The representative layer configuration of the emitting unit is given below.

(a) Hole-transporting layer/Emitting layer (/Electron-transporting layer)

(b) Hole-transporting layer/First phosphorescent emitting layer/Second phosphorescent emitting layer (/Electron-transporting layer)

(c) Hole-transporting layer/Phosphorescent emitting layer/Spacing layer/Fluorescent emitting layer (/Electron-transporting layer)

(d) Hole-transporting layer/First phosphorescent emitting layer/Second phosphorescent emitting layer/Spacing layer/Fluorescent emitting layer (/Electron-transporting layer)

(e) Hole-transporting layer/First phosphorescent emitting layer/Spacing layer/Second phosphorescent emitting layer/Spacing layer/Fluorescent emitting layer (/Electron-transporting layer)

(f) Hole-transporting layer/Phosphorescent emitting layer/Spacing layer/First fluorescent emitting layer/Second fluorescent emitting layer (/Electron-transporting layer)

(g) Hole-transporting layer/Electron barrier layer/Emitting layer (/Electron-transporting layer)

(h) Hole-transporting layer/Emitting layer/Hole barrier layer (/Electron-transporting layer)

(i) Hole-transporting layer/Fluorescent emitting layer/Triplet barrier layer (/Electron-transporting layer)

The phosphorescent or fluorescent emitting layer as mentioned above can emit different colors of light. Specifically, in the stacked emitting layer (d), a layer configuration of the hole transporting layer/first phosphorescent emitting layer (red emission)/second phosphorescent emitting layer (green emission)/spacing layer/fluorescent emitting layer (blue emission)/electron transporting layer or the like can be given.

Between each emitting layer and the hole-transporting layer or the spacing layer, an electron barrier layer may be provided appropriately. Between each emitting layer and the electron transporting layer, a hole-barrier layer (a hole blocking layer) may be provided appropriately.

Due to provision of an electron-barrier layer or a hole-barrier layer, electrons or holes can be confined within the emitting layer, whereby possibility of recombination of carriers in the emitting layer can be increased, and the life can be improved.

As the represented device configuration of a tandem organic EL device, the following device configuration can be given.

(2) Anode/First Emitting Unit/Intermediate Layer/Second Emitting Unit/Cathode

Here, as the first emitting unit and the second emitting unit, the same emitting units as those mentioned above can independently be given, for example.

In general, the intermediate layer is called an intermediate electrode, an intermediate conductive layer, a carrier-generating layer, an electron-withdrawing layer, and a known material configuration that supplies electrons to the first emitting unit and supplies holes to the second emitting unit can be used.

FIG. 1 shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole injecting and transporting layer 6 or the like may be provided between the emitting layer 5 and the anode 3 and an electron-injecting layer 8 and an electron transporting layer 7 or the like (electron injecting and transporting unit 11) may be provided between the emitting layer 5 and the cathode 4.

An electron-barrier layer may be provided on the anode 3 side of the emitting layer 5 and a hole-barrier layer may be provided on the cathode 4 side of the emitting layer 5.

Due to such configuration, electrons or holes can be confined in the emitting layer 5, whereby possibility of generation of excitons in the emitting layer 5 can be improved.

Herein, a host that is combined with a fluorescent dopant is referred to as a fluorescent host and a host that is combined with a phosphorescent dopant is referred to as a phosphorescent host. The fluorescent host and the phosphorescent host are not distinguished only by the molecular structure thereof. That is, the phosphorescent host means a material constituting a phosphorescent emitting layer that contains a phosphorescent dopant and does not mean a material that cannot be used as a material constituting a fluorescent dopant. The same can be applied to a fluorescent host.

Substrate

The organic EL device is usually formed on a transparent substrate. The transparent substrate is a substrate for supporting the organic EL device, and is preferably a flat and smooth substrate having a 400-to-700-nm-visible-light transmittance of 50% or more. Specific examples thereof include glass plates and polymer plates. Examples of the glass plate include those obtained by using as raw materials soda-lime glass, barium/strontium-containing glass, lead glass, aluminosilicate glass, borosilicate glass, barium borosilicate glass, quartz, or the like. Examples of the polymer plate include those obtained by using as raw materials polycarbonate, acrylic polymer, polyethylene terephthalate, polyethersulfide, polysulfone, or the like.

Anode

The anode of the organic EL device plays a role for injecting holes into its hole-transporting layer or emitting layer. It is effective to use one having a work function of 4.5 eV or more. As specific examples of the anode material, indium tin oxide alloy (ITO), tin oxide (NESA), indium zinc oxide, gold, silver, platinum, copper, and the like can be given. The anode can be formed by forming these electrode materials into a thin film by vapor deposition, sputtering or the like. In the case where emission from the emitting layer is taken out through the anode, the transmittance of the anode to the emission is preferably more than 10%. The sheet resistance of the anode is preferably several hundred Ω/E or less. The film thickness of the anode, which varies depending upon the material thereof, is usually from 10 nm to 1 μm, preferably from 10 to 200 nm.

Cathode

The cathode plays a role for injecting electrons into its electron-injecting layer, electron-transporting layer or emitting layer. The cathode is preferably formed of a material having a small work function. The cathode material is not particularly restricted. As specific examples of the cathode material, indium, aluminum, magnesium, a magnesium-indium alloy, a magnesium-aluminum alloy, an aluminum-lithium alloy, an aluminum-scandium-lithium alloy, a magnesium-silver alloy or the like can be given. As in the case of the anode, the cathode can be formed by forming the materials into a thin film by a deposition method, a sputtering method or the like. If necessary, emission can be outcoupled from the cathode side.

Emitting Layer

The present invention relates—in one embodiment—to an organic electroluminescence device, wherein the light emitting layer comprises at least one compound of formula (I).

The emitting layer is an organic layer having an emitting function, and where a doping system is used, it usually comprises a host material and a dopant material.

The host material has a function of accelerating recombination of electrons and holes and confining excitons within the emitting layer. The dopant material has a function of emitting efficiently excitons obtained by recombination.

In the case of a phosphorescent device, the host material has a function of confining excitons mainly generated by a dopant within the emitting layer.

Here, in the emitting layer, a double host (also referred to as a host/cohost) that adjusts the carrier balance in the emitting layer may be used by combining an electron-transporting host and a hole-transporting host or by other methods. It is preferred that the emitting layer comprise a first host material and a second host material and that at least one component of the first host material and the second host material is the compounds of the formula (I) according to the invention.

Double dopant may be used in which two or more types of dopant materials having a high quantum yield are incorporated, and each dopant emits light. Specifically, by allowing a host, a red dopant and a green dopant to be co-deposited, yellow emission from the common emitting layer, whereby yellow emission is realized.

As for the emitting layer, by allowing plural emitting layers to be a stacked body, electrons and holes are accumulated in the interface of the emitting layers, whereby the recombination region is concentrated in the interface of the emitting layers. As a result, the quantum efficiency is improved.

Easiness in injection of holes to the emitting layer and easiness in injection of electrons to the emitting layer may differ. Further, the hole-transporting performance and the electron transporting performance indicated by the mobility of holes and electrons in the emitting layer may differ from each other.

The emitting layer can be formed by a known method such as a deposition method, a spin coating method, a LB method (Langmuir Blodgett method) or the like, for example. The emitting layer can also be formed by forming a solution obtained by dissolving a binder such as a resin and material compounds in a solvent into a thin film by a spin coating method and the like.

The emitting layer is preferably a molecular deposited film. The "molecular deposited film" means a thin film formed by deposition of a raw material compound in a vapor phase or a film formed by solidification of a raw material compound in a solution state or a liquid phase state. Normally, this molecular deposited film differs from a thin film (molecular accumulated film) formed by a LB method in aggregation structure or high-order structure, or differ in function derived from such difference in structure.

In a more preferred embodiment, the light-emitting layer is formed from 0.1 to 70% by weight, preferably 1 to 30% by weight, of at least one of the emitter materials and 30 to 99.9% by weight, preferably 70 to 99% by weight, of at least one of the matrix materials mentioned in the specification—in one embodiment at least one compound of the formula (I)—where the sum total of the emitter material and of the matrix material adds up to 100% by weight.

(1) Phosphorescent Emitting Layer

The phosphorescent emitting layer usually comprises at least one emitter material and at least one host material. The phosphorescent host is a compound which confines the triplet energy of the phosphorescent dopant efficiently in the light emitting layer to cause the phosphorescent dopant to emit light efficiently.

A host material for phosphorescent emitting layer is usually selected from known phosphorescent host materials. Specific examples of the preferable phosphorescent host are, nitrogen-containing heteroaromatics, such as, indole derivatives, carbazole derivatives, pyridine derivatives, pyrimidine derivatives, triazine derivatives, quinoline derivatives, isoquinoline derivatives, quinazoline derivatives, nitrogenated-dibenzothiophene derivatives, nitrogenated-dibenzofuran derivatives, imidazole derivatives, such as benzimidazole derivatives, imidazopyridine derivatives, Benzimidazophenanthridine derivatives, benzimidzobenzimidazole derivatives; oxygen or sulfur containing heteroaromatics, such as thiophene derivatives, furan derivatives, benzothiophene derivatives, benzofuran derivatives, dibenzothiophene derivatives, dibenzofuran derivatives; aryl or heteroaryl substituted amine derivatives; metal complexes; aromatic hydrocarbon derivatives, such as benzene derivatives naphthalene derivatives, phenanthrene derivatives, triphenylene derivatives, fluorene derivatives, and so on, preferably, nitrogen containing heteroaromatics, the most preferably, the compounds of the formula (I).

According to one embodiment, the light-emitting layer comprises at least one emitter material and at least two matrix materials, wherein one of the matrix materials is a compound of the formula (1) and the other matrix material(s) is/are used as co-host(s). Suitable other host materials than the compounds of formula (1) (co-hosts) are mentioned below.

However, it is also possible to use two or more different compounds of formula (1) as host material in the light-emitting layer in an OLED of the present application.

Said second host material is selected from general phosphorescent host materials. Specific examples are selected from above mentioned derivatives, preferably, nitrogen containing heteroaromatics, more preferably, following general formula (N–1). The present invention therefore further relates to an organic electroluminescence device, wherein the light emitting layer comprises a heterocyclic derivative represented by the general formula (N–1) and preferably at least one compound of formula (1).

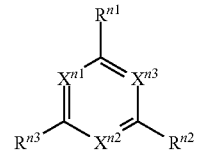

(N-1)

$X^{n1}$ to $X^{n3}$ each independently represents $CR^{n4}$ or N, $R^{n1}$ to $R^{n4}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, in the case of at least one of $X^{n1}$ to $X^{n3}$ represent $CR^{n4}$, two or more substituents selected among $R^{n1}$ to $R^{n4}$ may be bonded to each other to form a ring structure.

In one embodiment of the present invention, preferable heteroaromatics for the second host is specific nitrogen containing heteroaromatics with electron donating nitrogen atom(s), such as pyrrole derivatives, indole derivatives, carbazole derivatives, acridine derivatives, phenoxadine derivatives, phenothiazine derivatives, imidazole derivatives, benzimidazole derivatives, benzimidazobenzimidazole derivatives and so on, which may have additional substituents and additional fused ring structures, preferably carbazole derivatives, more preferably following general formula (P-1).

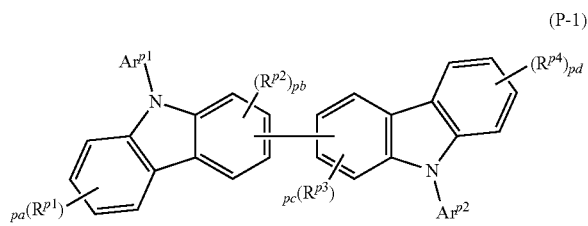

(P-1)

$Ar^{p1}$ and $Ar^{p2}$ each independently represents a substituted or unsubstituted aryl group having 6 to 24 carbon atoms, preferably, phenyl group, biphenyl group, terphenyl group, quarterphenyl group, naphthyl group, phenanthryl group or triphenylenyl group, or a substituted or unsubstituted heterocyclic group having 5 to 30 cyclic atoms, preferably, carbazoryl group, dibenzofuranyl group or dibenzothiophenyl group, or a substituent which consists of substituted or unsubstituted aryl group and substituted or unsubstituted heteroaryl group, preferably, aryl group and dibenzofuran group, aryl group and dibenzothiophene group or aryl group and carbazole group.

$R^{p1}$ to $R^{p4}$ each independently represents halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, a substituted phosphoryl group or a cyano group, or $R^{50}$ and $R^{51}$ may be bonded to each other to form a substituted or unsubstituted aryl group having 6 to 24 carbon atoms.

pa and pd each independently represents 0 to 4.
pb and pc each independently represents 0 to 3.

In one embodiment of the present invention, aryl or heteroaryl substituted amine derivatives can be preferably used for the second host material. Latter mentioned materials for hole transporting layer can be preferably used as a second host material.

In one embodiment of the present invention, fused aryl derivatives or fused heteroaryl derivatives are preferable for the second host material.

According to another embodiment, the light-emitting layer comprises at least one emitter material and at least two matrix materials (host materials), wherein one of the matrix materials is a material selected from the above mentioned known host materials and the other matrix material(s) is/are used as co-host(s). Suitable other host material(s) is/are selected from before mentioned general host materials.

In said embodiment, the light-emitting layer is formed from 0.1 to 70% by weight, preferably 1 to 30% by weight, of the at least one emitter material and 30 to 99.9% by weight, preferably 70 to 99% by weight, of a first host and the further matrix material, where the sum total of the at least one emitter material, the further matrix materials adds up to 100% by weight.

The content ratio of the compound of the first host material and the second matrix material as co-host in the light emitting layer is not particularly limited and may be selected accordingly, and the ratio of first host material: second host material is preferably 1:99 to 99:1, more preferably 10:90 to 90:10, each based on mass.

A phosphorescent dopant (phosphorescent emitting material) that forms the emitting layer is a compound that can emit light from triplet excited state. The phosphorescent dopant is not limited as long as it can emit from triplet excited state. The phosphorescent dopant is preferably an organic metal complex containing at least one metal selected from Ir, Pt, Os, Au, Cu, Re and Ru and a ligand. It is preferred that the ligand have an ortho-metalated bond. In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex, with an ortho-metalated complex being more preferable. Among them, an iridium complex and a platinum complex are more preferable, and an ortho-metalated iridium complex is particularly preferable.

The phosphorescent host is a compound having a function of allowing a phosphorescent dopant to emit light efficiently by efficiently confining the triplet energy of the phosphorescent dopant in the emitting layer. The material for an organic EL device according to the invention is preferable as the phosphorescent host. The emitting layer may comprise one kind of the material for an organic EL device according to the invention or may comprise two or more kinds of the material for an organic EL device according to the invention.

When the material for an organic EL device according to the invention is used as a host material of the emitting layer, the emission wavelength of the phosphorescent dopant contained in the emitting layer is not particularly restricted. It is preferred that at least one kind of the phosphorescent dopant materials contained in the emitting layer have a peak of an emission wavelength of 490 nm or more and 700 nm or less, more preferably 490 nm or more and 650 nm or less. As for the emission color of the emitting layer, red, yellow and green are preferable, for example. By using the compound according to the invention as the host material and by forming an emitting layer by doping the phosphorescent dopant having such an emission wavelength, it is possible to obtain a long-lived organic EL device.

In the organic EL device according to the invention, other compounds than the material for an organic EL device according to the invention can appropriately be selected as the phosphorescent host according to the above-mentioned purpose.

The material for an organic EL device according to the invention and other compounds may be used in combination as the phosphorescent host material in the same emitting layer.

When plural emitting layers are present, as the phosphorescent host material for one of these emitting layers, the material for an organic EL device according to the invention is used, and as the phosphorescent host material for one of other emitting layers, other compounds than the material for an organic EL device according to the invention may be used. The material for an organic EL device according to the invention can be used in an organic layer other than the emitting layer. In that case, as the phosphorescent host of the emitting layer, other compounds than the material for an organic EL device according to the invention may be used.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass.

Suitable metal complexes (dopants, especially phosphorescent dopants) for use in the inventive OLEDs, preferably as emitter material, are described as following general formula (E-1).

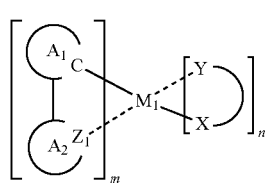

(E-1)

Wherein $M_1$ is a metal having an atomic weight greater than 40, preferably, Ir, Pt, Pd, Rh, Re, Ru, Os, TI, Pb, Bi, In, Sn, Sb, Te, Au, or Ag, more preferably Ir, Pt, or Os, most preferably Ir, $A_1$ represents aryl group having 6 to 24 carbon atoms or heterocyclic group having 3 to 24 cyclic atoms, preferably above mentioned substituents which may have additional substituents, $A_2$ represents nitrogen containing heterocyclic group having 3 to 24 cyclic atoms, preferably above mentioned substituents which may have additional substituents, $Z_1$ represents C or N, preferably N, (X-Y) is an ancillary ligand, preferably acetylacetonate derivatives, picolinate derivatives, more preferably acetylacetonate derivatives, m is a value from 1 to the maximum number of ligands that may be attached to the metal; and m+n is the maximum number of ligands that may be attached to the metal.

If m or n is more than 2, two or more ligands may be the same or different in each occurrence.

According to one embodiment, a metal complex represented by the following general formula (E-2) is more preferable especially for green and yellow emitter,

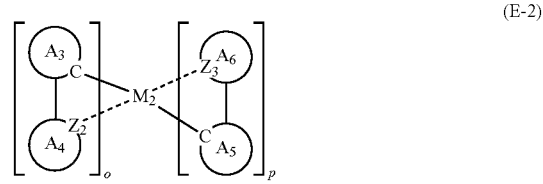

(E-2)

Wherein $M_2$ is a metal having an atomic weight greater than 40, preferably, Ir, Pt, Pd, Rh, Re, Ru, Os, TI, Pb, Bi, In, Sn, Sb, Te, Au, or Ag, more preferably Ir, Pt, or Os, most preferably Ir, $A_3$, $A_5$ each independently represents aryl group having 6 to 24 carbon atoms or heterocyclic group having 3 to 24 cyclic atoms, preferably above mentioned substituents which may have additional substituents, $A_4$, $A_6$ each independently represents nitrogen containing heterocyclic group having 3 to 24 cyclic atoms, preferably above mentioned substituents which may have additional substituents, $Z_2$, $Z_3$ each independently represents C or N, preferably N, o is a value from 1 to the maximum number of ligands that may be attached to the metal; and o+p is the maximum number of ligands that may be attached to the metal.

If o or p is more than 2, two or more ligands may be the same or different in each occurrence.

A metal complex represented by the following general formula (T) or (β) is more preferable.

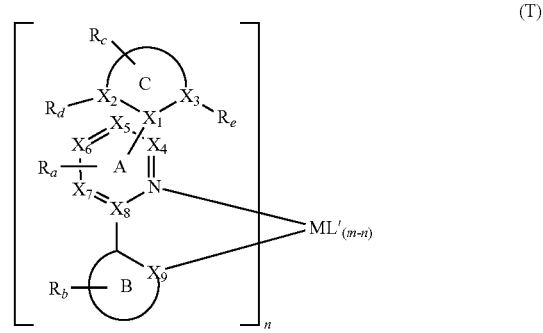

(T)

M represents the above mentioned metal atom,

B, C each independently represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, A represents a nitrogen containing 6 membered ring structure which may have additional substituents, preferably pyridine, pyrimidine, more preferably pyridine, X4 to X8 each represents C or N, preferably C, m represents oxidation state of the metal M, n is 1 or greater than 1, L' represents following chemical structure,

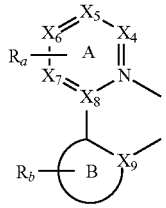

(L')

wherein A represents nitrogen containing 6 membered ring structure which may have additional substituents, preferably pyridine, pyrimidine, more preferably pyridine, B represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, X9 represents C or N, preferably, N.

$R^a$, $R^b$, $R^c$ or $R^d$ each independently represents hydrogen, a substituted or unsubstituted alkyl group having 1 to 25 carbon atoms, a substituted or unsubstituted alkoxy group having 1 to 25 carbon atoms, a substituted or unsubstituted amino group, a substituted or unsubstituted alkenyl group having 2 to 25 carbon atoms, a substituted or unsubstituted alkynyl group having 2 to 25 carbon atoms, a substituted or unsubstituted aralkyl group having 7 to 24 carbon atoms, a substituted or unsubstituted aryl group having 6 to 24 carbon atoms or a substituted or unsubstituted heterocyclic group having 5 to 30 cyclic atoms,

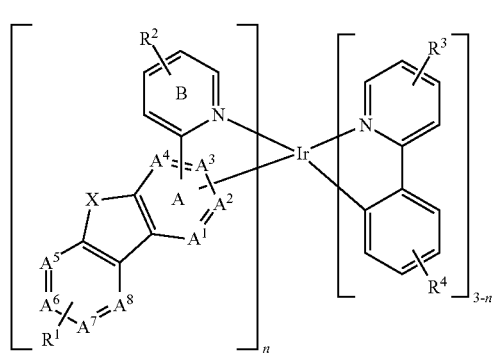

(β)

Wherein X represents NR, oxygen atom, sulfur atom, BR or Selenium atom, R represents hydrogen atom, a substituted or unsubstituted alkyl group having 1 to 25 carbon atoms, $A^1$ to $A^8$ independently represents CH, $CR^5$ or N, preferably CH or $CR^5$, $R^1$ to $R^5$ each independently represents a substituted or unsubstituted alkyl group having 1 to 25 carbon atoms, a substituted or unsubstituted aryl group having 6 to 24 ring carbon atoms, n is 1, 2 or 3, preferably 1.

In another embodiment, a metal complex represented by any one of the following general formula (V), (X), (Y), (Z) can be used.

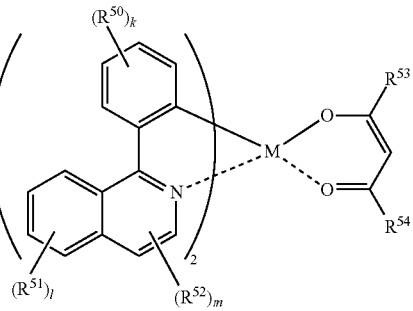

(V)

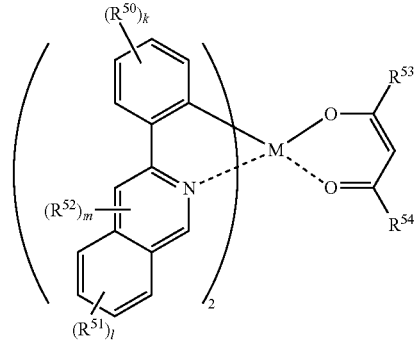

(X)

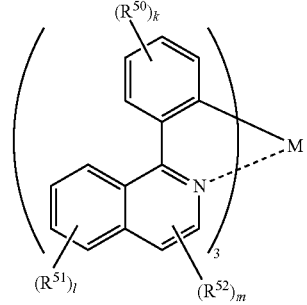

(Y)

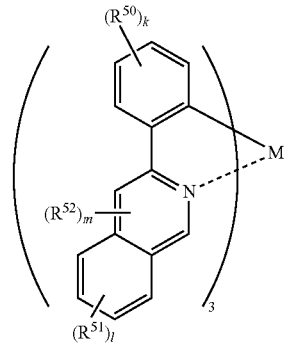

(Z)

Wherein $R^{50}$ to $R^{52}$ each represents a substituted or unsubstituted alkyl group having 1 to 25 carbon atoms, a substituted or unsubstituted aryl group having 6 to 24 ring carbon atoms, k is 0, 1, 2, 3 or 4, m is 0, 1 or 2, l is 0, 1, 2, 3 or 4, M represents iridium atom (Ir), osmium atom (Os) or platinum atom (Pt).

Formula (V) is preferably represented by formula (V-1). Formula (X) is preferably represented by formula (X-1) or (X-2).

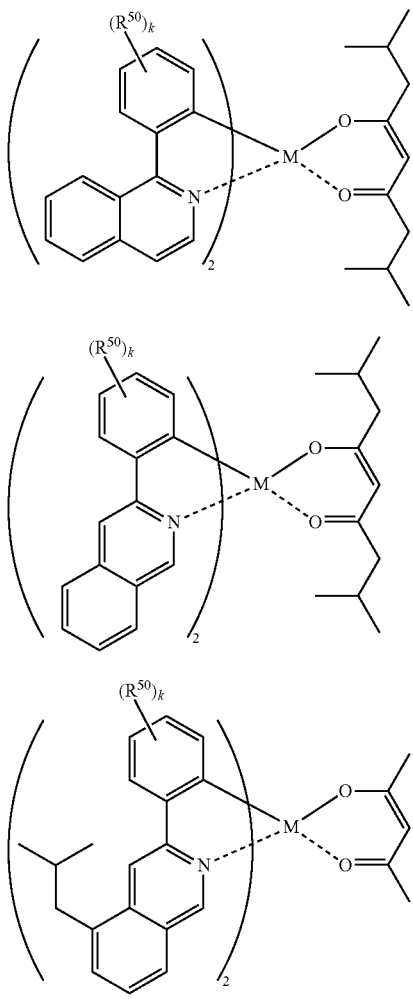

(V-1)

(X-1)

(X-2)

Wherein R^50, M and k are as defined in formula (V) and (X).

(2) Fluorescent Emitting Layer

The fluorescent emitting layer usually comprises at least one emitter material and at least one host material.

A host material for fluorescent emitting layer is usually selected from general host materials, which preferably have wider band-gap than the emitter material to get highly efficient light emission from the emitter through energy transfer mechanism from the excited host to the emitter. Specific examples of the preferable fluorescent host are, substituted or unsubstituted above mentioned heterocyclic compound; or substituted or unsubstituted aromatic hydrocarbon compound, such as oligo-phenylene derivatives, naphthalene derivatives, fluorene derivatives, fluoranthene derivatives, anthracene derivatives, phenanthrene derivatives, pyrene derivatives, triphenylene derivatives, benzanthracene derivatives, chrysene derivatives, benzphenanthrene derivatives, naphthacene derivstives, benzochrysene derivatives, and so on, preferably anthracene derivatives, pyrene derivatives and naphthacene derivatives, more preferably, anthracene derivatives represented by following general formula (X) especially for fluorescent blue or green device.

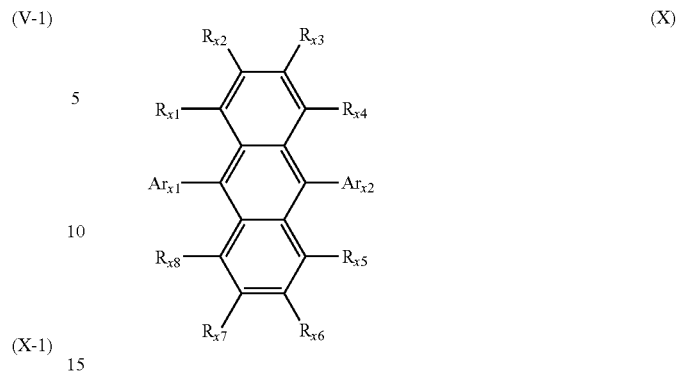

(X)

$Ar_X^1$ and $Ar_{X2}$ are independently a substituted or unsubstituted aryl group including 6 to 50 ring carbon atoms, preferably phenyl group, biphenyl group, naphthyl group, phenanthryl group, fluorenyl group, fluoranthenyl group, anthryl group, pyrenyl group, benzphenanthryl group, triphenylenyl group, benzanthryl group, benzochrysenyl group, or a heterocyclic group including 5 to 50 ring atoms, preferably, benzofuranyl group, benzothiophenyl group, indolyl group, dibenzothiophenyl group, dibenzofuranyl group, carbazolyl group, benzocarbazoryl group, dibenzocarbazoryl group, indolophenanthryl group, naphthobenzofuranyl group, naphthobenzothiophenyl group, dinaphthofuranyl group, dinaphthothiophenyl group, benzophenanthlofuranyl group, benzophenanthlothiophenyl group, benzofurodibenzofuranyl group, benzothiodibenzothiophenyl group, benzofurodibenzotihiophenyl group, benzothiodibenzofuranyl group, more preferably oxygen or sulfer containing heteroaromatics, such as furan or thiophene containing heteroaromatics in one of the part of the heteroaromatics. $R_X^1$ to $R_{X8}$ are independently a hydrogen atom, a substituted or unsubstituted aryl group including 6 to 50 ring carbon atoms, a substituted or unsubstituted heterocyclic group including 5 to 50 ring atoms, an alkyl group including 1 to 50 carbon atoms, a substituted or unsubstituted alkoxy group including 1 to 50 carbon atoms, a substituted or unsubstituted aralkyl group including 7 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, a substituted or unsubstituted silyl group, a carboxy group, a halogen atom, a cyano group, a nitro group or a hydroxyl group. Preferred host materials for the fluorescent emitting layer are the compounds of the formula (1) (as single hosts or as co-hosts).

An emitter material for fluorescent emitting layer is usually selected from general emitter materials or fluorescent dyes, which preferably have high absorption co-efficiency and high quantum efficiency to get highly efficient light emission from the emitter. Specific examples of the preferable fluorescent emitter are, aromatic hydrocarbon derivatives, such as oligo-phenylene derivatives, naphthalene derivatives, fluorene derivatives, fluoranthenyl group, fused fluoranthenyl group, anthracene derivatives, phenanthrene derivatives, pyrene derivatives, triphenylene derivatives, benzanthracene derivatives, chrysene derivatives, benzphenanthrene derivatives, naphthacene derivstives, benzochrysene derivatives, and so on; aromatic or heterocyclic amine derivatives represented by following general formula (Y); organic boron derivatives represented by general formula (Z),

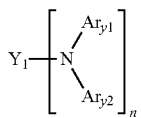
(Y)

$Y_1$ is a substituted or unsubstituted aromatic hydrocarbon group including 6 to 50 ring carbon atoms, preferably fused aromatic hydrocarbon group, or substituted or unsubstituted heterocyclic group having 5 to 50 cyclic atoms.

$Ar_{y1}$ and $Ar_{y2}$ are independently a substituted or unsubstituted aryl group including 6 to 50 ring carbon atoms or a substituted or unsubstituted heterocyclic ring group including 5 to 50 ring atoms, preferably, oxygen or sulfur containing heterocyclic group.

Specific examples of $Y_1$ include the above-mentioned fused aryl group. $Y_1$ is preferably a substituted or unsubstituted anthryl group; a substituted or unsubstituted pyrenyl group; a substituted or unsubstituted chrysenyl group; substituted or unsubstituted fluorenyl group, especially substituted or unsubstituted mono-, di-, or tri-benzofuro-fused fluorene, or substituted or unsubstituted mono-, di-, or tri-benzothio-fused fluorene; substituted or unsubstituted dibenzofuran containing heterocyclic group; substituted or unsubstituted dibenzothiophene containing heterocyclic group.

n is an integer of 1 to 4, preferably 1 or 2.

Electron-Transporting Layer

The electron-transporting layer is an organic layer that is formed between the emitting layer and the cathode and has a function of transporting electrons from the cathode to the emitting layer. When the electron-transporting layer is formed of plural layers, an organic layer that is nearer to the cathode is often defined as the electron-injecting layer. The electron-injecting layer has a function of injecting electrons from the cathode efficiently to the organic layer unit.

According to one embodiment, it is preferred that an electron-transporting layer further comprises the other one or more layer(s) than electron injection layer to enhance efficiency and lifetime of the device, preferably between an electron injection layer and an emitting layer as a hole blocking layer, a exciton blocking layer or a triplet blocking layer.

A compound of the formula (1) is also preferable as all the use of the electron transporting layer, such as an electron transporting layer, an electron-injecting layer, a hole blocking layer, a exciton blocking layer or a triplet blocking layer.

According to one embodiment, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them, K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work function: 2.52 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as $Li_2O$, $Cs_2O$ or $K_2O$, and an alkali halide such as LiF, NaF, CsF and KF. Among them, LiF, $Li_2O$ and NaF are preferable. Examples of the alkaline earth metal compound include BaO, SrO, CaO, and mixtures thereof such as $Ba_xSr_{1-x}O$ (0<x<1) and $Ba_xCa_{1-x}O$ (0<x<1). Among them, BaO, SrO and CaO are preferable. Examples of the rare earth metal compound include $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound: the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

The ratio of the main component and the electron-donating dopant in the organic EL device according to the invention is main component: electron-donating dopant=5:1 to 1:5 in terms of molar ratio, more preferably 2:1 to 1:2.

As the electron-transporting material used in the electron-transporting layer other than a compound of the formula (I), an aromatic heterocyclic compound having one or more hetero atoms in the molecule may preferably be used. In particular, a nitrogen containing heterocyclic derivative is preferable.

According to one embodiment, it is preferable that the electron-transporting layer comprises a nitrogen containing heterocyclics metal chelate, such as 8-hydroxyquinolinolato aluminum, which is generally called as Alq$_3$.

According to the other embodiment, it is preferable that the electron-transporting layer comprising substituted or unsubstituted nitrogen containing heterocyclic derivative.

Specific examples of the preferable heterocyclic derivative for the electron-transporting layer are, 6-membered azine derivatives; such as pyridine derivatives, pyrimidine derivatives, triazine derivatives, pyrazine derivatives, preferably pyrimidine derivatives or triazine derivatives; 6-membered fused azine derivatives, such as quinolone derivatives, isoquinoline derivatives, quinoxaline derivatives, quinazoline derivatives, phenanthroline derivatives, benzoquinoline derivatives, benzoisoquinoline derivatives, dibenzoquinoxaline derivatives, preferably quinolone derivatives, isoquinoline derivatives, phenanthroline derivatives; 5-membered heterocyclic derivatives, such as imidazole derivatives, oxazole derivatives, oxadiazole derivatives, triazole derivatives, thiazole derivatives, thiadiazole derivatives; fused imidazole derivatives, such as benzimidazole derivatives, imidazopyridine derivatives, naphthoimidazole derivatives, benzimidazophenanthridine derivatives, benzimidzobenzimidazole derivatives, preferably benzimidazole derivatives, imidazopyridine derivatives or benzimidazophenanthridine derivatives.

According to the other embodiment, it is preferable the electron-transporting layer comprises phosphine oxide derivative represented as $Ar_{p1}Ar_{p2}Ar_3P=O$.

$Ar_{p1}$ to $Ar_{p3}$ are the substituents of phosphor atom and each independently represent substituted or unsubstituted above mentioned aryl group or substituted or unsubstituted above mentioned heterocyclic group.

According to the other embodiment, it is preferable that the electron-transporting layer comprises aromatic hydrocarbon derivatives.

Specific examples of the preferable aromatic hydrocarbon derivatives for the electron-transporting layer are, oligophenylene derivatives, naphthalene derivatives, fluorene derivatives, fluoranthenyl group, anthracene derivatives, phenanthrene derivatives, pyrene derivatives, triphenylene derivatives, benzanthracene derivatives, chrysene derivatives, benzphenanthrene derivatives, naphthacene derivsatives, benzochrysene derivatives, and so on, preferably anthracene derivatives, pyrene derivatives and fluoranthene derivatives.

The present invention therefore relates to an organic electroluminescence device, wherein an electron transporting layer is provided between the cathode and the light emitting layer, and the electron transporting layer comprises at least one compound of formula (1).

The present invention therefore further relates to an organic electroluminescence device, wherein a hole blocking layer is provided between the electron transporting layer and the light emitting layer, and the hole blocking layer comprises at least one compound of formula (1).

According to one embodiment, it is preferred that the other electron transporting region is further comprised between the hole blocking layer comprising the compound of general formula (1) and cathode. Said electron transporting region generally comprises one or more electron transporting layer(s).

Above mentioned electron injection materials, such as alkali metal compound or alkali metal complex, preferably comprising as one of electron transporting layer at the interface of cathode.

Second electron transporting layer preferably comprises between hole blocking layer and said electron transporting layer comprising electron injection material.

Above mentioned heterocyclic derivatives or fused aromatic derivatives are preferably used for second electron transporting layer, more preferably heterocyclic derivatives represented by general formulae (ET-1), (ET-2), (ET-3) or (ET-4).

(ET-1)

$X^{e1}$ to $X^{e3}$ each independently represents $CR^{e4}$ or N, preferably more than two of $X^{e1}$ to $X^{e3}$ are N, $R^{e1}$ to $R^{e4}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, in the case of at least one of $X^{e1}$ to $X^{e3}$ represent $CR^{e4}$, two or more substituents selected among $R^{e1}$ to $R^{e4}$ may be bonded to each other to form a ring structure.

(ET-2)

$X^{e5}$ to $X^{e10}$ each independently represents $CR^{e5}$ or N, preferably at least $X^{e6}$ is N, $Y^{e1}$ represents oxygen atom, sulfur atom, $CR^{e6}R^{e7}$ or $NR^{e8}$, $R^{e5}$ to $R^{e8}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, two or more substituents selected among $R^{e5}$ to $R^{e8}$ may be bonded to each other to form a ring structure.

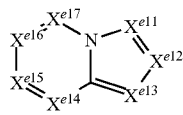

(ET-3)

$X^{e11}$ to $X^{e17}$ each independently represents $CR^{e9}$ or N, preferably at least one selected from $X^{e11}$, $X^{e12}$ and $X^{e13}$ is N, $R^{e9}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, two or more substituents selected among $R^{e9}$ may be bonded to each other to form a ring structure.

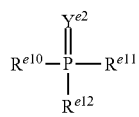

(ET-4)

$R^{e11}$ to $R^{e12}$ each independently represents a substituted or unsubstituted aryl group having 6 to 24 carbon atoms, a substituted or unsubstituted heterocyclic group having 5 to 30 cyclic atoms, two or more substituents selected among $R^{e11}$ to $R^{e12}$ may be bonded to each other to form a ring structure, preferably at least one of $R^{e10}$ to $R^{e12}$ have additional substituted or unsubstituted aryl group having 6 to 24 carbon atoms, or substituted or unsubstituted heterocyclic group having 5 to 30 cyclic atoms, $Y^{e2}$ represents oxygen atom or sulfur atom.

Hole-Transporting Layer

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode.

Said hole injection layer is generally used for stabilizing hole injection from anode to hole transporting layer which is generally consist of organic materials.

Organic material having good contact with anode or organic material with β-type doping is preferably used for the hole injection layer.

Acceptor materials, or fused aromatic hydrocarbon materials or fused heterocycles which have high planarity, are preferably used, acceptor materials are more preferably used for the hole injection layer.

Specific examples for acceptor materials are, the quinone derivatives with one or more electron withdrawing groups, such as $F_4TCNQ$(2,3,5,6-tetrafluoro-7,7,8,8-tetracyanoquinodimethane), 1,2,3-Tris[(cyano)(4-cyano-2,3,5,6-tetrafluorophenyl)methylene]cyclopropane, and so on; hexa-azatriphenylene derivatives with one or more electron withdrawing groups, such as hexa-azatriphenylene-hexanitrile; aromatic hydrocarbon derivatives with one or more electron withdrawing groups; aryl boron derivatives with one or more electron withdrawing groups, and so on.

β-doping is usually consist of one or more β-dopant materials and one or more matrix materials. Matrix materials preferably have shallower HOMO level and β-dopant preferably have deeper LUMO level to enhance the carrier density of the layer. Aryl or heteroaryl amine derivatives are preferably used as the matrix materials. Specific examples for the matrix material are the same as that for hole transporting layer which is explained at the later part. Specific examples for β-dopant are the above mentioned acceptor materials, preferably the quinone derivatives with one or more electron withdrawing groups, such as $F_4TCNQ$, 1,2, 3-Tris[(cyano)(4-cyano-2,3,5,6-tetrafluorophenyl)methylene]cyclopropane.

The ratio of the β-type dopant is preferably less than 20% of molar ratio, more preferably less than 10%, such as 1%, 3%, 5% and so on.

Hole transporting layer is generally used for injecting and transporting holes efficiently, and aromatic or heterocyclic amine derivatives are preferably used.

Specific examples for hole transporting layer are represented as general formula (H),

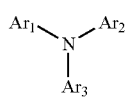

(H)

$Ar_1$ to $Ar_3$ each independently represents substituted or unsubstituted aryl group having 5 to 50 carbon atoms or substituted or unsubstituted heterocyclic group having 5 to 50 cyclic atoms, preferably phenyl group, biphenyl group, terphenyl group, naphthyl group, phenanthryl group, triphenylenyl group, fluorenyl group, spirobifluorenyl group, indenofluorenyl group, carbazolyl group, dibenzofuranyl group, dibenzothiophenyl group, carbazole substituted aryl group, dibenzofuran substituted aryl group or dibenzothiophene substituted aryl group; two or more substituents selected among $Ar^1$ to $Ar^3$ may be bonded to each other to form a ring structure, such as carbazole ring structure, acridane ring structure and so on.

According to one embodiment, it is preferable that at least one of $Ar_1$ to $Ar_3$ have additional one aryl or heterocyclic amine substituent, more preferably $Ar_1$ has an additional aryl amino substituent, at the case of that it is preferable that $Ar_1$ represents substituted or unsubstituted biphenylene group, substituted or unsubstituted fluorenylene group.

A second hole transporting layer is preferably inserted between the first hole transporting layer and the emitting layer to enhance device performance by blocking excess electrons or excitons. Specific examples for second hole transporting layer is the same as the first hole transporting layer. It is preferably that second hole transporting layer have higher triplet energy to block triplet exciton especially for phosphorescent green device, such as bicarbazole derivatives, biphenylamine derivatives, triphenylenyl amine derivatives, fluorenyl amine detrivatives, carbazole substituted arylamine derivatives, dibenzofuran substituted arylamine derivatives, dibenzothiophene substituted arylamine derivatives, and so on.

Spacing Layer

The spacing layer is a layer provided between the fluorescent emitting layer and the phosphorescent emitting layer when the fluorescent emitting layer and the phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is provided between the emitting layers, the material for the spacing layer is preferably a material having both electron-transporting properties and hole-transporting properties. In order to prevent diffusion of the triplet energy in adjacent phosphorescent emitting layers, it is preferred that the spacing layer have a triplet energy of 2.6 eV or more. As the material used for the spacing layer, the same material as those used in the above-mentioned hole-transporting layer can be given.

Barrier Layer

It is preferred that the organic EL device according to the invention have a barrier layer such as an electron-barrier layer, a hole-barrier layer and a triplet barrier layer in a part that is adjacent to the emitting layer. Here, the electron-barrier layer is a layer that serves to prevent leakage of electrons from the emitting layer to the hole-transporting layer, and the hole-barrier layer is a layer that serves to prevent leakage of holes from the emitting layer to the electron-transporting layer.

The triplet barrier layer prevents diffusion of triplet excitons generated in the emitting layer to the surrounding layers, and has a function of preventing energy deactivation of triplet excitons on molecules in the electron-transporting layer other than the emitting dopant by confining the triplet excitons within the emitting layer.

When the triplet barrier layer is provided, in the phosphorescent emitting device, the following is considered. The triplet energy of the phosphorescent emitting dopant is taken as $E^T_d$ and the triplet energy of the compound used as the triplet barrier layer is taken as $E^T_{TB}$. If the energy relationship $E^T_d < E^T_{TB}$ is satisfied, in respect of energy, the triplet excitons of the phosphorescent emitting dopant is confined (i.e. the triplet excitons cannot be moved to other molecules), whereby the energy deactivation route other than emission on the dopant is cut off, leading to efficient emission. However, even when the relationship $E^T_d < E^T_{TB}$ is established, if the energy difference $\Delta E^T = E^T_{TB} - E^T_d$ is small, it is thought that, in an environment at around room temperature where the device is actually driven, due to thermal energy of the surrounding area, the triplet excitons can move to other molecules by endothermically overcoming this energy difference $\Delta E^T$. In particular, in the case of phosphorescent emission that has a longer exciton life as compared with fluorescent emission, effects of the endothermic move of excitons relatively tend to appear. Relative to the thermal energy at room temperature, a larger energy difference $\Delta E^T$ is preferable. The energy difference $\Delta E^T$ is further preferably 0.1 eV or more, and particularly preferably 0.2 eV or more. On the other hand, in a fluorescent device, as the triplet barrier layer of the TTF device configuration disclosed in WO2010/134350A1, the inventive compounds of formula (I) can be used.

The electron mobility of the material constituting the triplet barrier layer is desirably $10^{-6}$ cm$^2$/Vs or more in a field intensity range of 0.04 to 0.5 MV/cm. As the method for measuring the electron mobility of an organic material, several methods that include the Time of Flight method are known. Here, the electron mobility means an electron mobility that is determined by the impedance spectroscopy.

The electron mobility of the electron-injecting layer is desirably $10^{-6}$ cm$^2$/Vs or more in a field intensity range of 0.04 to 0.5 MV/cm. The reason is that, by this electron mobility, injection of electrons from the cathode to the electron-transporting layer is promoted, and as a result, injection of electrons to adjacent barrier layer and emitting layer is promoted, enabling the device to be driven at a lower voltage.

The present invention further relates to an electronic equipment comprising the organic electroluminescence device according to the present invention.

The organic EL device using the inventive compounds of formula (1) can be used as an emitting device in a panel module used in various displays.

The organic EL device using the inventive compounds of formula (1) can be used as a display element of a TV, a mobile phone and a PC; or an electronic apparatus such as lightings or the like.

The OLEDs (organic EL devices) can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

I Synthesis Examples

Synthesis Example 1

Synthesis Example 1-1

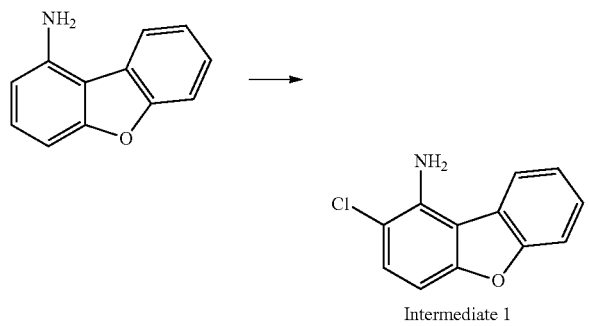

Intermediate 1

In a nitrogen flushed 500 ml three-necked round-bottomed flask 1-aminodibenzofuran (9.2 g, 50 mmol) was dissolved in carbon tetrachloride (250 ml) under nitrogen. N-chlorosuccinimide (6.3 g, 47.5 mmol) was added to the reaction mixture. The reaction mixture was heated to 90° C. with an oil bath for 2 hours. The solvent was evaporated and the residue was dissolved in methyl tert-butyl ether and then washed with water and brine. The crude product was added to a silica gel column and was eluted with heptane and toluene to give 8.9 g of white solid (82% yield). The identification of the intermediate 1 was made by FD-MS (field desorption mass spectrometry) analysis.

Synthesis Example 1-2

Intermediate 1

Intermediate 2

In a nitrogen flushed 1000 ml three-necked round-bottomed flask intermediate 1 (6.5 g, 30 mmol), 2-bromo-9,9-dimethylfluorene (6.8 g, 25 mmol), (±)-2,2'-bis(diphenylphosphino)-1,1'-binaphthalene (1.5 g, 2.4 mmol), palladium(II) acetate (0.27 g, 1.2 mmol) and sodium tert-butoxide (5.77 g, 60 mmol) were dissolved in xylene under nitrogen. The reaction mixture was heated 145° C. with an oil bath for 5 hours. The reaction mixture was diluted with ethyl acetate, and the insoluble salts were filtrated. The organic phase was washed with water. The crude product was added to a silica gel column and was eluted with heptane and toluene and to give 8.85 g of white solid (86% yield). The identification of the intermediate 2 was made by FD-MS (field desorption mass spectrometry) analysis.

Synthesis Example 1-3

Intermediate 2

Intermediate 3

In a nitrogen flushed 350 ml three-necked round-bottomed flask intermediate 2 (8.2 g, 20 mmol), tricyclohexylphosphine tetrafluoroborate (1.2 g, 3.2 mmol), palladium(II) acetate (0.36 g, 1.6 mmol) and potassium carbonate (5.5 g, 40 mmol) were dissolved in N,N-dimethylacetamide under nitrogen. The reaction mixture was heated 145° C. with an oil bath for 22 hours. The reaction mixture was filtrated and the most of N,N-dimethylacetamide was evaporated. Water was added to the crude product followed by extraction with ethyl acetate and then washed with water. The crude product was added to a silica gel column and was eluted with heptane and toluene and to give 4.28 g of yellow solid (57% yield). The identification of the intermediate 3 was made by FD-MS (field desorption mass spectrometry) analysis.

Synthesis Example 1-4

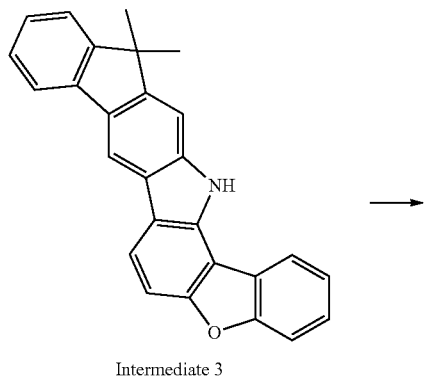

Intermediate 3

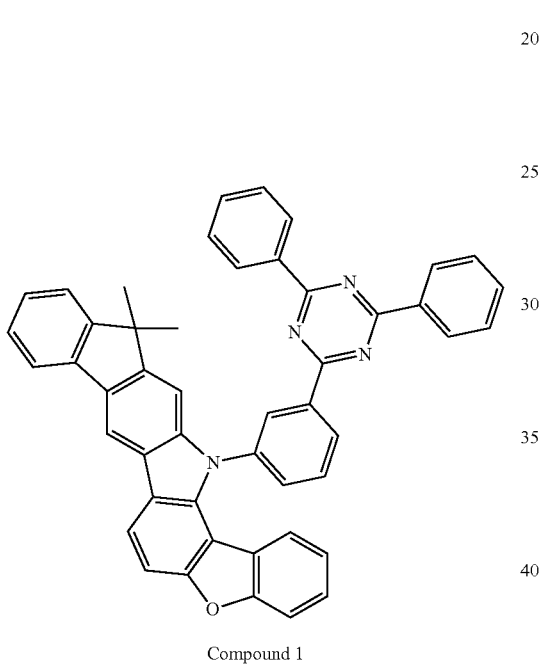

Compound 1

In a nitrogen flushed 100 ml three-necked round-bottomed flask intermediate 3 (1.5 g, 4.2 mmol), 2-(3-bromophenyl)-4,6-diphenyl-1,3,5-triazine (1.6 g, 4.2 mmol), 4,5-bis(diphenylphosphino)-9,9-dimethylxanthene (0.1 g, 0.17 mmol), tris(dibenzylideneacetone)dipalladium(0) (0.077 g, 0.084 mmol) and sodium tert-butoxide (1.2 g, 12.6 mmol) were dissolved in xylene under nitrogen. The reaction mixture was heated 145° C. with an oil bath for 3 hours. The reaction mixture was diluted with methanol, and the precipitate solid was filtrated then washed with methanol and water. The crude product was added to a silica gel column and was eluted with heptane and toluene and to give 2.33 g of white solid (90% yield).

The compound was measured for FD-MS (field desorption mass spectrometry), maximum ultraviolet absorption wavelength (UV(PhMe) λmax) in toluene, and maximum fluorescence wavelength (FL (PhMe, λex=350 nm) λmax) in toluene. The result is shown below.

FDMS: calcd. for C48H32N4O=680, found m/z=680 (M+)

FL (PhMe, λex=350 nm) λmax: 482 nm

Synthesis Example 2-1

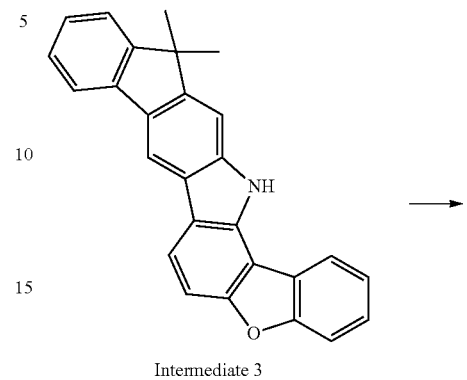

Intermediate 3

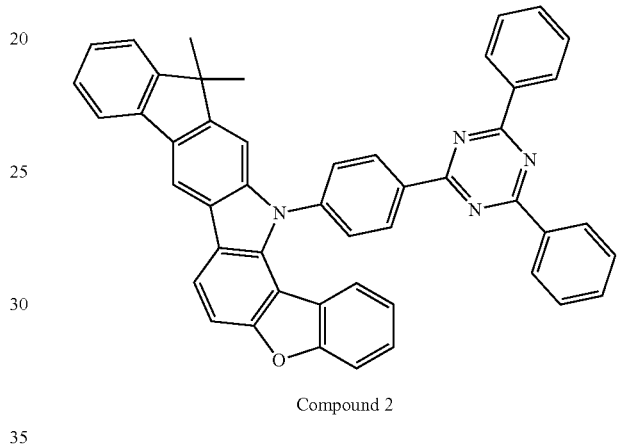

Compound 2

The procedure of the synthesis of compound 1 was repeated except for using 2-(4-bromophenyl)-4,6-diphenyl-1,3,5-triazine in place of 2-(3-bromophenyl)-4,6-diphenyl-1,3,5-triazine. The compound was measured for FD-MS (field desorption mass spectrometry) and maximum fluorescence wavelength (FL (PhMe, λex=350 nm) λmax) in toluene. The result is shown below.

FDMS: calcd. for C48H32N4O=680, found m/z=680 (M+)

FL (PhMe, λex=350 nm) λmax: 462 nm

Synthesis Example 3-1

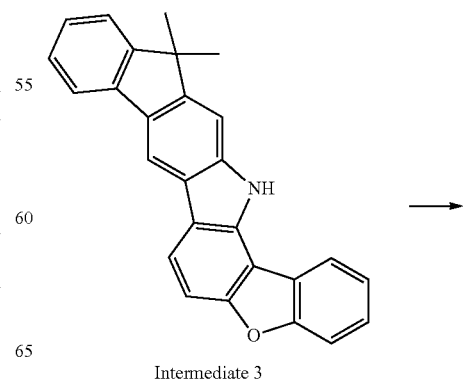

Intermediate 3

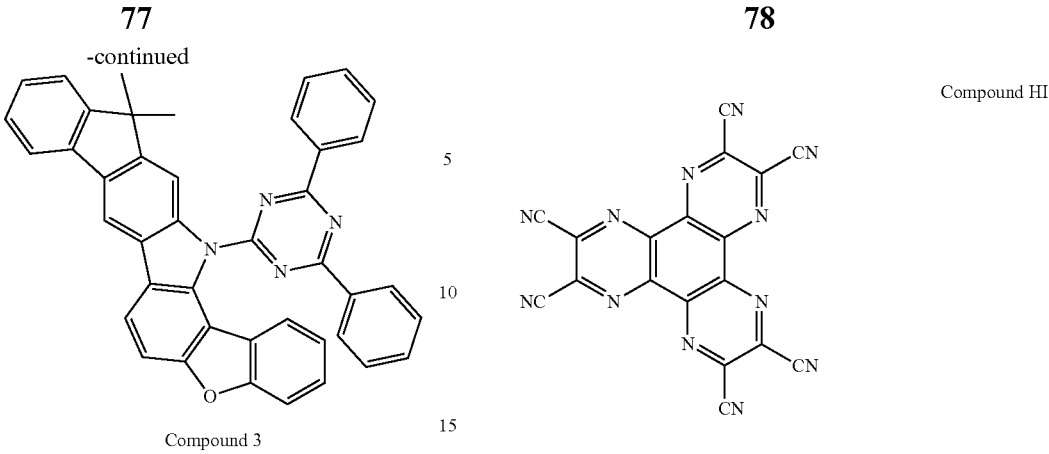

Compound 3

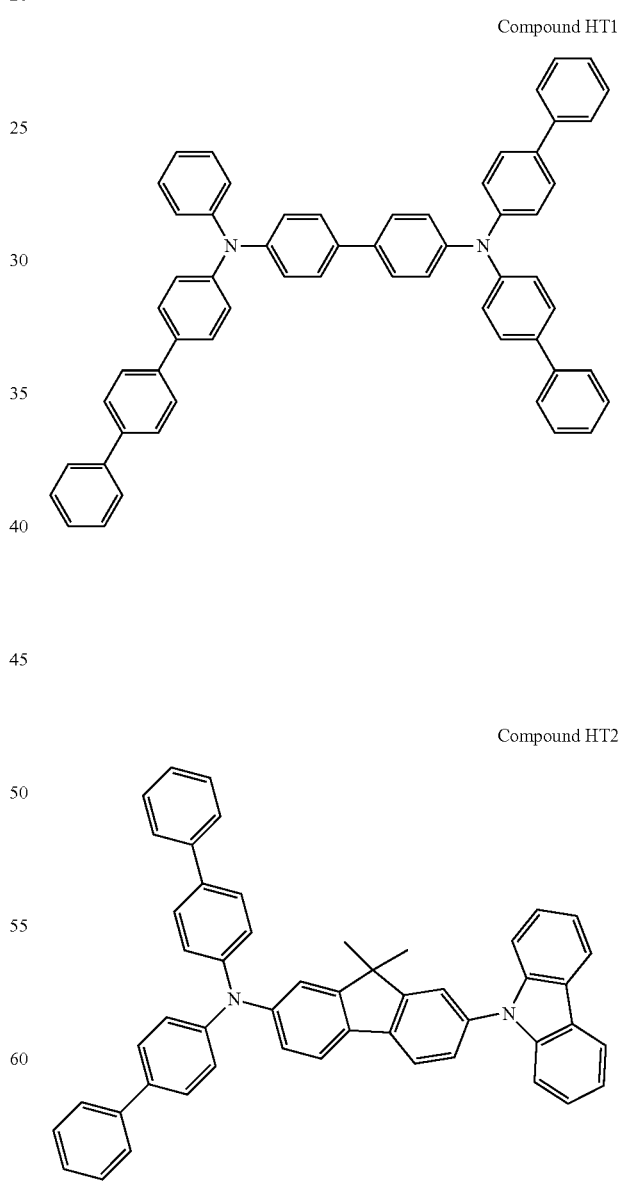

The procedure of the synthesis of compound 1 was repeated except for using 2-chloro-4,6-diphenyl-1,3,5-triazine in place of 2-(3-bromophenyl)-4,6-diphenyl-1,3,5-triazine. The compound was measured for FD-MS (field desorption mass spectrometry) and maximum fluorescence wavelength (FL (PhMe, λex=350 nm) λmax) in toluene. The result is shown below.

FDMS: calcd. for C42H28N4O=604, found m/z=604 (M+)

FL (PhMe, λex=350 nm) λmax: 529 nm

II Application Example

Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound HI was applied. Then 100 nm-thick of compound HT1 and 60 nm-thick compound HT2 were applied as hole transporting layer 1 and hole transporting layer 2, respectively. Subsequently, a mixture of 5% by weight of an emitter compound (tris[2-phenylpyridinato-$C^2$,N])iridium (III), 47.5% by weight of a host (compound 1) and 47.5% by weight of compound PH1 were applied to form a 40 nm-thick phosphorescent-emitting layer. On the emitting layer, 30 nm-thick compound ET was applied as an electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. In addition, the current-voltage characteristic was measured in combination with the luminance to determine luminous efficiency and external quantum efficiency (EQE). Driving voltage (Voltage) is given at a current density of 10 mA/cm². The device results are shown in Table 1.

-continued
Compound 1
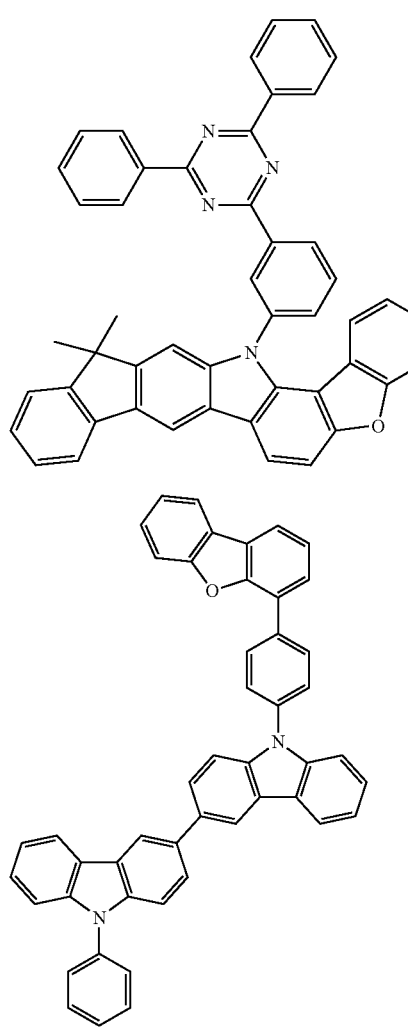
Compound PH1
Compound ET
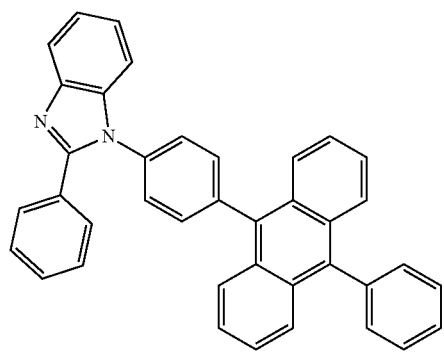
Comparative Application Example 1
Application Example 1 was repeated except for using the compound shown in place of the host (compound 1). The device result is shown in Table 1.
TABLE 1
| Appl. Ex. | Host | Voltage [V] | CIE(x, y) |
| --- | --- | --- | --- |
| Appl. Ex. 1 | Compound 1 | 4.9 | 0.31, 0.63 |
| Comp. Appl. Ex. 1 | Comparative Compound 1 | 5.2 | 0.31, 0.63 |
Comparative Compound 1
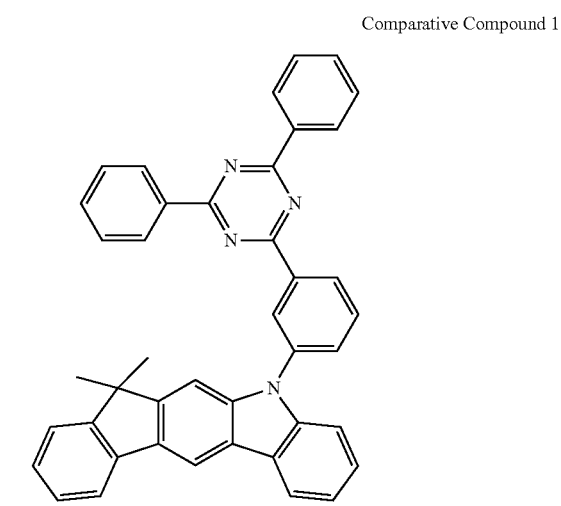
Comparative Compound 2
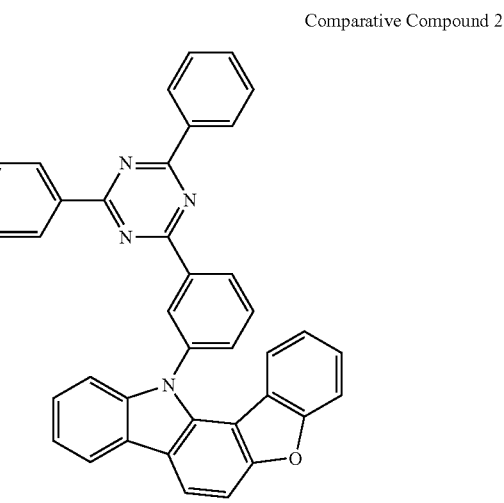

-continued

Comparative Compound 3

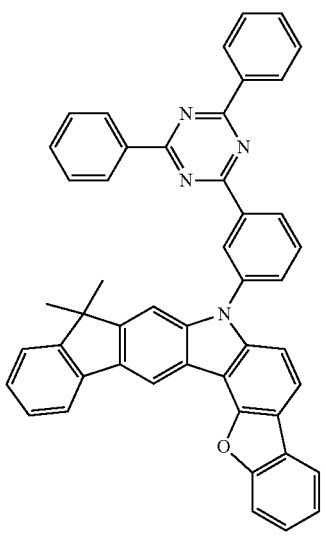

Compound PH2

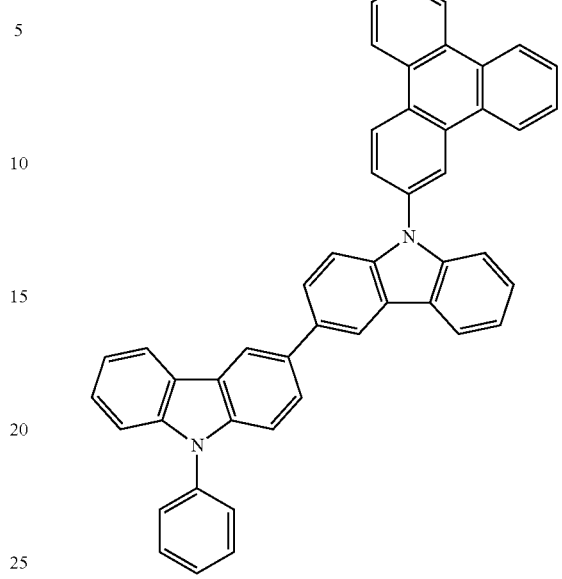

The results shown in Table 1 demonstrate that the voltage was improved in the case that an inventive compound 1 was used as green hosts together with a co-host Compound PH1 in an OLED.

Application Example 2

Application Example 1 was repeated except for using a host compound PH2 in place of the host (compound PH1). The device result is shown in Table 2.

Comparative Application Examples 2-4

Application Example 2 was repeated except for using each compound shown in table 2 in place of the host (compound 1). The device results are shown in Table 2.

To characterize the OLED, electroluminescence spectra were recorded at various currents and voltages. In addition, the current-voltage characteristic was measured in combination with the luminance to determine luminous efficiency and external quantum efficiency (EQE). Driving voltage (Voltage) is given at a current density of 10 mA/cm², and 80% lifetime (LT80), the time spent until the initial luminance at 50 mA/cm² is reduced to 80%, is recorded. The device results are shown in Table 2.

Comparative Compound 4

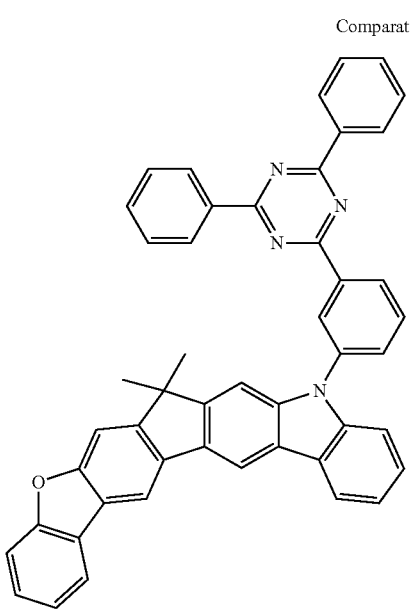

TABLE 2

| Appl. Ex. | Host | Voltage [V] | LT80 [hrs] | CIE(x, y) |
|---|---|---|---|---|
| Appl. Ex. 2 | Compound 1 | 4.9 | 160 | 0.31, 0.63 |
| Comp. Appl. Ex. 2 | Comparative Compound 2 | 5.4 | 50 | 0.32, 0.63 |
| Comp. Appl. Ex. 3 | Comparative Compound 3 | 5.3 | 100 | 0.31, 0.63 |
| Comp. Appl. Ex. 4 | Comparative Compound 4 | 5.2 | 90 | 0.31, 0.63 |

The results shown in Table 2 demonstrate that the lifetime and voltage were improved in the case that an inventive compound 1 was used as a green host together with a co-host Compound PH2 in anOLED.

Application Example 3, Comparative Application Example 5

Application Example 1 was repeated except for using the compounds shown in the Table 3 in place of the hosts compound 1 and PH1. The device result is shown in Table 3.

TABLE 3

| Appl. Ex. | Host 1 | Host 2 | Voltage [V] | CIE(x, y) |
|---|---|---|---|---|
| Appl. Ex. 3 | Compound 2 | PH3 | 4.9 | 0.31, 0.63 |
| Comp. Appl. Ex. 5 | Comparative Compound 1 | PH3 | 5.2 | 0.31, 0.63 |

Application Example 4, Comparative Application Example 6

Application Example 1 was repeated except for using the compounds shown in the Table 4 in place of the hosts compound 1 and PH1.

To characterize the OLED, electroluminescence spectra were recorded at various currents and voltages. In addition, the current-voltage characteristic was measured in combination with the luminance to determine luminous efficiency and external quantum efficiency (EQE). Driving voltage (Voltage) is given at a current density of 10 mA/cm$^2$, and 80% lifetime (LT80), the time spent until the initial luminance at 50 mA/cm$^2$ is reduced to 80%, is recorded. The device results are shown in Table 4.

TABLE 4

| Appl. Ex. | Host 1 | Host 2 | Voltage [V] | LT80 [hrs] | CIE(x, y) |
|---|---|---|---|---|---|
| Appl. Ex. 4 | Compound 3 | PH3 | 5.0 | 140 | 0.31, 0.63 |
| Comp. Appl. Ex. 6 | Comparative Compound 5 | PH3 | 5.4 | 60 | 0.31, 0.63 |

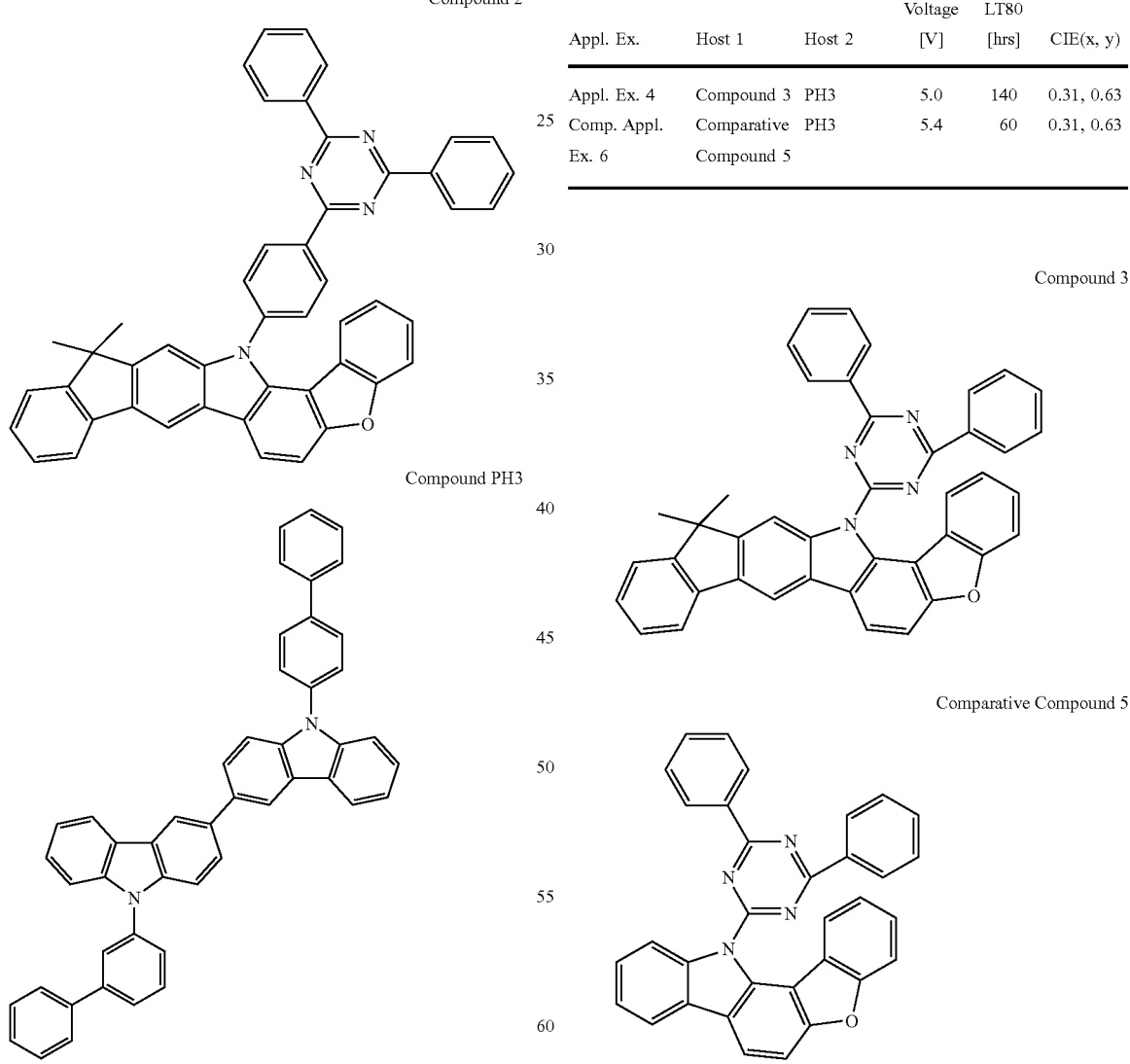

The results shown in Table 3 demonstrate that the voltage was improved in the case that an inventive compound 2 was used as green hosts together with a co-host Compound PH3 in an OLED.

The results shown in Table 4 demonstrate that the lifetime and voltage were improved in the case that an inventive compound 3 was used as a green host together with a co-host Compound PH3 in anOLED.

The invention claimed is:

1. A compound of formula (I):

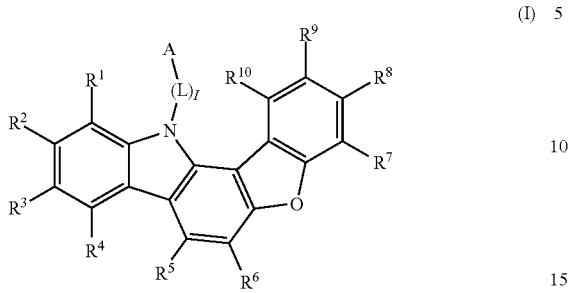

(I)

wherein

R$^1$, R$^2$, R$^3$ and R$^4$ are each independently hydrogen or R$^a$, with proviso that a pair of two substituents selected from R$^2$ and R$^3$, and R$^3$ and R$^4$ is linked to one another and forms a group of formula (II):

(II)

wherein

Ar$_1$ represents a substituted or unsubstituted aromatic hydrocarbon group having 6 to 30 ring carbon atoms or a substituted or unsubstituted heterocyclic group having 5 to 30 ring atoms;

dotted lines are bonding sites;

R$^5$, R$^6$, R$^7$, R$^8$, R$^9$, R$^{10}$, R$^{15}$, R$^{16}$ and R$^a$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

R$^{15}$ and R$^{16}$ are optionally bonded to each other to form a ring structure;

two or more substituents selected from R$^a$, R$^5$, R$^6$, R$^7$, R$^8$, R$^9$ and R$^{10}$ are optionally bonded to each other to form a ring structure;

A is a substituted or unsubstituted aromatic hydrocarbon group having 6 to 30 ring carbon atoms; or a substituted or unsubstituted heterocyclic group having 5 to 30 ring atoms, or a disubstituted amino group;

L is a single bond, a substituted or unsubstituted alkylene group having 1 to 30 carbon atoms, a substituted or unsubstituted cycloalkylene group having 3 to 30 carbon atoms, a substituted divalent silyl group having 2 to 30 carbon atoms, a substituted or unsubstituted divalent aromatic hydrocarbon group having 6 to 30 ring carbon atoms, or a substituted or unsubstituted divalent heterocyclic group having 5 to 30 ring atoms; and l is 0, 1, 2 or 3.

2. The compound according to claim 1, wherein the group of formula (II) is represented by formula (IIb):

(IIb)

wherein

Q$^1$ is CR$^{11}$ or N; Q$^2$ is CR$^{12}$ or N; Q$^3$ is CR$^{13}$ or N and Q$^4$ is CR$^{14}$ or N;

dotted lines are bonding sites;

R$^{11}$, R$^{12}$, R$^{13}$ and R$^{14}$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group; and two or more substituents selected from $R^{11}$, $R^{12}$, $R^{13}$ and $R^{14}$ are optionally bonded to each other to form a ring structure.

3. The compound according to claim 1,
wherein the compound is represented by a formula selected from the following formulae(Ic-1a), (Id-1a); (Ie-1a) and (If-1a):

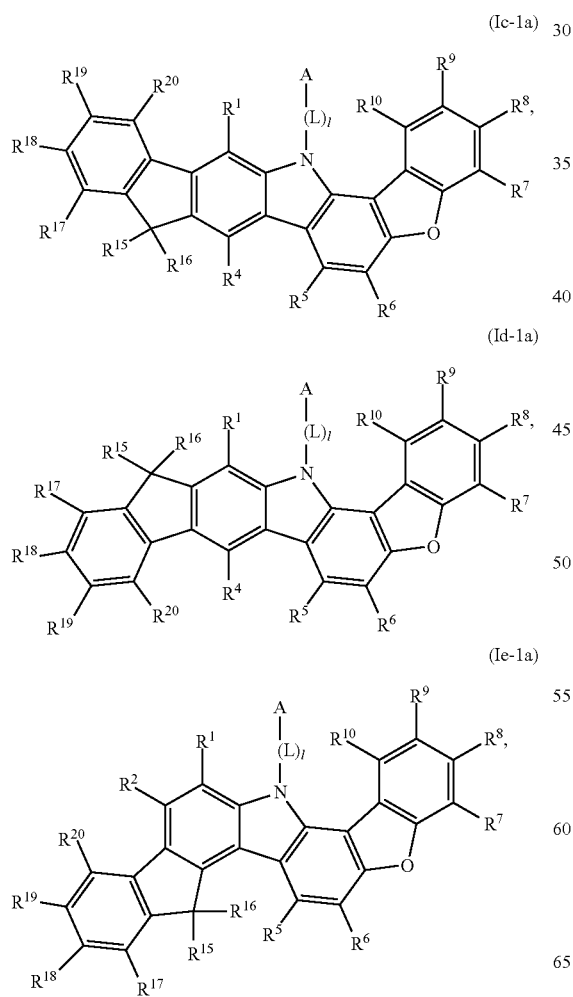

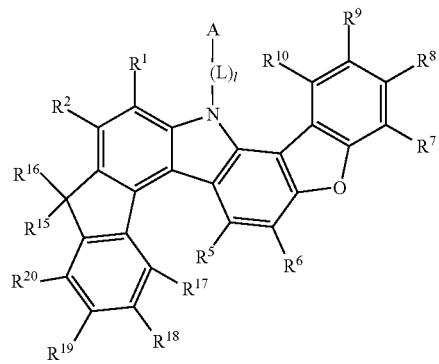

wherein
$R^{17}$, $R^{18}$, $R^{19}$ and $R^{20}$ are each independently hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; a di-substituted amino group having a substituent selected from a group consisting of a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms; a substituted or unsubstituted alkoxy group having 1 to 30 carbon atoms; a substituted or unsubstituted alkylthio group having 1 to 30 carbon atoms; a substituted or unsubstituted aryloxy group having 6 to 30 ring carbon atoms; a substituted or unsubstituted arylthio group having 6 to 30 ring carbon atoms; a mono-, di-, or tri-substituted silyl group having a substituent selected from a group consisting of a substituted or unsubstituted alkyl group having 1 to 30 carbon atoms and a substituted or unsubstituted aromatic hydrocarbon group having 6 to 30 ring carbon atoms; a substituted or unsubstituted heterocyclic group having 5 to 30 ring atoms; a halogen atom; a cyano group; a nitro group; a sulfonyl group having a substituent selected from a group consisting of a substituted or unsubstituted alkyl group having 1 to 30 carbon atoms and a substituted or unsubstituted aromatic hydrocarbon group having 6 to 30 ring carbon atoms; a di-substituted phosphoryl group having a substituent selected from a group consisting of a substituted or unsubstituted alkyl group having 1 to 30 carbon atoms and a substituted or unsubstituted aromatic hydrocarbon group having 6 to 30 ring carbon atoms; an alkylcarbonyloxy group having 2 to 31 carbon atoms; an arylcarbonyloxy group having 6 to 30 ring carbon atoms; or a boron-containing group;

two or more substituents selected from $R^{17}$, $R^{18}$, $R^{19}$ and $R^{20}$ are optionally bonded to each other to form a ring structure;

is a single bond, a substituted or unsubstituted alkylene group having 1 to 30 carbon atoms, a substituted or unsubstituted cycloalkylene group having 3 to 30 carbon atoms, a substituted divalent silyl group having 2 to 30 carbon atoms, a substituted or unsubstituted divalent aromatic hydrocarbon group having 6 to 30 ring carbon atoms, or a substituted or unsubstituted divalent heterocyclic group having 5 to 30 ring atoms, and l is 0,1,2 or 3.

4. The compound according to claim 1,
wherein A is represented by formula (III)

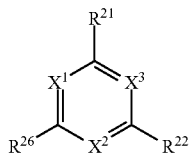
(III)

wherein
$X^1$, $X^2$ and $X^3$ each independently represent $CR^{23}$ or an N atom, wherein each $R^{23}$ are optionally the same or different: and $R^{21}$, $R^{22}$, $R^{23}$ and $R^{26}$ each independently represent hydrogen, a halogen atom, a substituted or unsubstituted alkyl group having 1 to 30 carbon atoms, a substituted or unsubstituted alkenyl group having 2 to 31 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, provided that, among $R^{21}$, $R^{22}$, $R^{26}$ and $R^{23}$, if $X^1$, $X^2$ and/or $X^3$ are $CR^{23}$, any two of $R^{21}$, $R^{22}$, $R^{23}$ and $R^{26}$ are optionally bonded each other to form ring structures; wherein one of $R^{21}$, $R^{22}$, $R^{26}$ and, if $X^1$, $X^2$ and/or $X^3$ are $CR^{23}$, $R^{23}$, represents a bonding site to -(L)$_l$-.

5. The compound according to claim 1,
wherein A is represented by a formula selected from (IIIa), (IIIb), (IIIc), (IIId), (IIIe), and (IIIf):

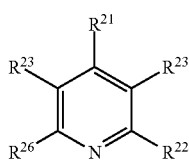
(IIIa)

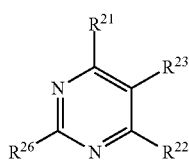
(IIIb)

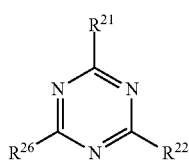
(IIIc)

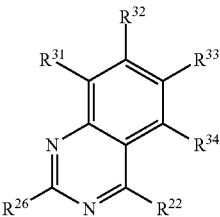
(IIId)

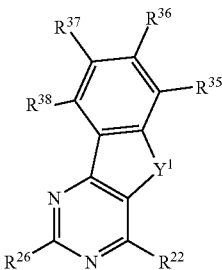
(IIIe)

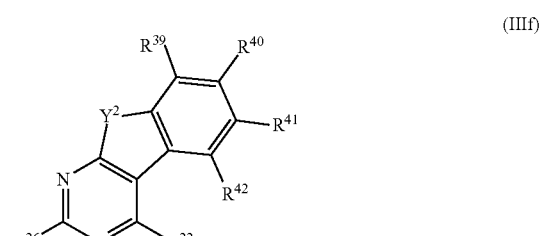
(IIIf)

wherein $Y^1$ and $Y^2$ each independently represent O, S, $NR^{43}$ or $CR^{44}R^{45}$; and $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ each independently represent hydrogen, a halogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, provided that, among from $R^{21}$, $R^{22}$, $R^{23}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$, any two of from $R^{21}$, $R^{22}$, $R^{23}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ are optionally bonded each other to form ring structures, wherein one of $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ represents a bonding site to -(L)$_l$-.

6. The compound according to claim 1 wherein is represented by formula (IVa):

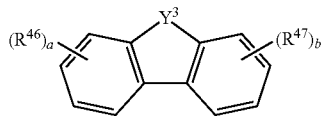

(IVa)

wherein
$Y^3$ represents O, S or $NR^{48}$;
$R^{46}$, $R^{47}$ and $R^{48}$ each independently represent a halogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group;
a is 0, 1, 2, 3 or 4; and
b is 0, 1, 2, 3 or 4,
when a is more than 1, the $R^{46}$s are optionally the same or different and are allowed to be bonded to each other to form a ring structure,
when b is more than 1, the $R^{47}$s are optionally the same or different and are allowed to be bonded to each other to form a ring structure,
wherein one of $R^{46}$, $R^{47}$ and $R^{48}$ represents a bonding site to $-(L)_f-$.

7. The compound according to claim 1,
wherein A represents a substituted or unsubstituted aromatic hydrocarbon group having 6 to 30 ring carbon atoms.

8. The compound according to claim 1,
wherein A represents a substituted or unsubstituted aromatic hydrocarbon group selected from the group consisting of phenyl, naphthyl, phenanthryl, triphenylenyl, fluorenyl and fluoranthenyl.

9. A material for an organic electroluminescence device comprising at least one compound according to claim 1.

10. An organic electroluminescence device which comprises an organic thin film layer between an anode and a cathode, wherein the organic thin film layer comprises one or more layers and comprises a light emitting layer, and at least one layer of the organic thin film layer comprises at least one compound according to claim 1.

11. The organic electroluminescence device according to claim 10, wherein the light emitting layer comprises the compound.

12. The organic electroluminescence device according to claim 10, wherein the light emitting layer comprises a phosphorescent material, which is an ortho-metallated complex comprising a metal atom selected from the group consisting of iridium, osmium and platinum.

13. The organic electroluminescence device according to claim 10, wherein an electron transporting layer is provided between the cathode and the light emitting layer, and the electron transporting layer comprises the compound.

14. The organic electroluminescence device according to claim 10, wherein an electron transporting layer is provided between the cathode and the light emitting layer, and the electron transporting layer comprises the compound.

15. An electronic equipment comprising the organic electroluminescence device according to claim 10.

* * * * *